United States Patent
Hasebe et al.

(10) Patent No.: US 10,351,643 B2
(45) Date of Patent: Jul. 16, 2019

(54) POLYMERIZABLE COMPOUNDS, COMPOSITIONS, POLYMERS, OPTICALLY ANISOTROPIC ARTICLES, LIQUID CRYSTAL DISPLAY DEVICES AND ORGANIC EL DEVICES

(71) Applicant: DIC CORPORATION, Tokyo (JP)

(72) Inventors: Hiroshi Hasebe, Kita-adachi-gun (JP); Yoshio Aoki, Kita-adachi-gun (JP); Kunihiko Kotani, Kita-adachi-gun (JP); Akihiro Koiso, Kita-adachi-gun (JP); Hidetoshi Nakata, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 383 days.

(21) Appl. No.: 15/100,108

(22) PCT Filed: Nov. 27, 2014

(86) PCT No.: PCT/JP2014/081441
§ 371 (c)(1),
(2) Date: May 27, 2016

(87) PCT Pub. No.: WO2015/080218
PCT Pub. Date: Jun. 4, 2015

(65) Prior Publication Data
US 2017/0037159 A1 Feb. 9, 2017

(30) Foreign Application Priority Data

Nov. 29, 2013 (JP) .................... 2013-248382

(51) Int. Cl.
| | | |
|---|---|---|
| *G02F 1/1333* | (2006.01) | |
| *C08F 122/24* | (2006.01) | |
| *C07D 339/06* | (2006.01) | |
| *C07D 409/04* | (2006.01) | |
| *C08F 222/10* | (2006.01) | |
| *C09K 19/34* | (2006.01) | |
| *C09K 19/38* | (2006.01) | |
| *C09K 19/32* | (2006.01) | |
| *C07D 413/04* | (2006.01) | |
| *C07D 417/04* | (2006.01) | |
| *C07D 471/04* | (2006.01) | |
| *C09K 19/02* | (2006.01) | |
| *G02B 5/30* | (2006.01) | |
| *H01L 51/00* | (2006.01) | |
| *C09K 19/04* | (2006.01) | |
| *G02F 1/13363* | (2006.01) | |
| *H01L 51/52* | (2006.01) | |

(52) U.S. Cl.
CPC .......... *C08F 122/24* (2013.01); *C07D 339/06* (2013.01); *C07D 409/04* (2013.01); *C07D 413/04* (2013.01); *C07D 417/04* (2013.01); *C07D 471/04* (2013.01); *C08F 222/10* (2013.01); *C09K 19/02* (2013.01); *C09K 19/32* (2013.01); *C09K 19/34* (2013.01); *C09K 19/3483* (2013.01); *C09K 19/3486* (2013.01); *C09K 19/3491* (2013.01); *C09K 19/3497* (2013.01); *C09K 19/38* (2013.01); *C09K 19/3861* (2013.01); *G02B 5/3016* (2013.01); *H01L 51/004* (2013.01); *C08F 2222/1013* (2013.01); *C09K 2019/0448* (2013.01); *G02F 1/13363* (2013.01); *G02F 2001/133633* (2013.01); *H01L 51/0074* (2013.01); *H01L 51/5281* (2013.01)

(58) Field of Classification Search
CPC ........ C09K 19/02; C09K 19/32; C09K 19/34; C09K 19/3483; C09K 19/3486; C09K 19/3491; C09K 19/3497; C09K 19/38; C09K 19/3861; C09K 2019/0448; C07D 339/06; C07D 409/04; C07D 413/04; C07D 417/04; C07D 471/04; C08F 122/24; C08F 222/10; C08F 2222/1013; G02F 1/1333; G02F 1/13363; G02F 2001/133633; H01L 51/004; H01L 51/0074; H01L 51/5281; G02B 5/3016
USPC ........................................................ 526/257
See application file for complete search history.

(56) References Cited

U.S. PATENT DOCUMENTS

2017/0037159 A1* 2/2017 Hasebe ................ C07D 339/06

* cited by examiner

*Primary Examiner* — Geraldina Visonti
(74) *Attorney, Agent, or Firm* — Westerman, Hattori, Daniels & Adrian, LLP

(57) ABSTRACT

An object of the invention is to provide polymerizable compounds having excellent optical characteristics and suited as materials for optically anisotropic articles, compositions containing the polymerizable compounds, polymers obtained by polymerizing the polymerizable compounds, optically anisotropic articles formed of the polymers, and liquid crystal display devices including the optically anisotropic articles.

10 Claims, No Drawings

POLYMERIZABLE COMPOUNDS, COMPOSITIONS, POLYMERS, OPTICALLY ANISOTROPIC ARTICLES, LIQUID CRYSTAL DISPLAY DEVICES AND ORGANIC EL DEVICES

TECHNICAL FIELD

The present invention relates to polymerizable compounds, compositions, polymers, optically anisotropic articles, liquid crystal display devices and organic EL devices.

BACKGROUND ART

Optically anisotropic articles such as retardation films and polarizers used in liquid crystal displays may be produced by the application of a solution containing a polymerizable liquid crystal material onto a rubbed substrate or a substrate having an optical alignment layer, followed by drying of the solvent and UV or thermal polymerisation. To enhance the viewing angle of liquid crystal displays, retardation films are required to have a small or reverse wavelength dispersion of birefringence (Δn). To realize this characteristic, polymerizable liquid crystal compounds of reverse dispersion type have been developed (for example, Patent Literature 1). In general, a retardation film is said to have a reverse wavelength dispersion of birefringence or a polymerizable liquid crystal compound forming the retardation film is said to be of reverse dispersion type when a graph which plots the birefringence (Δn=refractive index $n_e$ at extraordinary light–refractive index $n_o$ at ordinary light) on the ordinate against the wavelength λ of the incident light on the abscissa has a positive slope (in which the magnitude of birefringence increases with increasing wavelength).

CITATION LIST

Patent Literature

PTL 1: Japanese Unexamined Patent Application Publication (Translation of PCT Application) No. 2013-509458

SUMMARY OF INVENTION

Technical Problem

One approach to giving reverse dispersion characteristics to a polymerizable compound for forming a retardation film is to introduce into the molecule a segment which has a larger birefringence in a direction perpendicular to the longer axis of the molecule (such a segment is also written as the vertical unit). However, the introduction of such vertical units tends to result in a decrease in liquid crystallinity or tends to facilitate crystallization. Because of this fact, much trial and error are necessary in order to obtain polymerizable compounds that have desired characteristics.

The present invention has been made in light of the circumstances discussed above. It is therefore an object of the invention to provide polymerizable compounds having excellent optical characteristics and suited as materials for optically anisotropic articles, compositions containing the polymerizable compounds, polymers obtained by polymerizing the polymerizable compounds, optically anisotropic articles formed of the polymers, and liquid crystal display devices including the optically anisotropic articles.

Solution to Problem

The first aspect of the present invention resides in the following polymerizable compound.

A polymerizable compound represented by the general formula (1-0):

[Chem. 1]

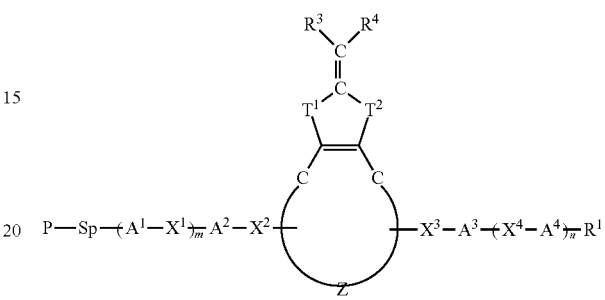

(1-0)

[in the formula (1-0), P is a polymerizable functional group, Sp is a spacer group or a single bond, $A^1, A^2, A^3$ and $A^4$ each independently represent a divalent alicyclic hydrocarbon group or aromatic hydrocarbon group, $X^1, X^2, X^3$ and $X^4$ each independently represent a divalent bonding group or a single bond, $R^1$ is an alkyl or alkoxy group having 1 to 12 carbon atoms, or "*-Sp-P" (* indicates $A^4$ or $A^3$), m and n are each independently an integer of 0 to 4 (wherein m+n is an integer of 2 or greater), Z in combination with C—C=C—C in the formula represents a naphthalene ring wherein the group including $X^2$ and the group including $X^3$ in the formula substitute for any two hydrogen atoms bonded to the naphthalene ring, $T^1$ and $T^2$ each independently represent —S—, —O—, —NR—, —CH$_2$—, —NH—, —C(=O)—, —S(=O)— or —C(=S)—, $R^2$ is a hydrogen atom, a halogen atom, an alkyl group having 1 to 6 carbon atoms, an alkoxy group having 1 to 6 carbon atoms, a cyano group, a nitro group or a hydroxyl group, $R^3$ and $R^4$ each independently represent a monovalent substituent or form a ring through Y which connects $R^3$ and $R^4$ together wherein when such a ring is formed, $R^3$ and $R^4$ each independently represent a group selected from the group consisting of —O—, —S—, —SO—, —SO$_2$—, —NR— (wherein R is a hydrogen atom or a monovalent substituent), =N—, =N(+)R— (wherein R is a hydrogen atom or a monovalent substituent), —C(=O)—, —C(=S)— and =CR— (wherein R is a hydrogen atom or a monovalent substituent), and Y represents 2 to 4 atoms selected from the group consisting of carbon atoms and Group XIV to Group XVI nonmetallic atoms, and in combination with $R^3$—C—$R^4$ in the formula forms a 5- to 7-membered ring which may be substituted with a monovalent substituent in place of any hydrogen atom bonded to the 5- to 7-membered ring, except when $T^1$ and $R^3$, and $T^2$ and $R^4$ are each the same as each other and when $T^1$ and $R^4$, and $T^2$ and $R^3$ are each the same as each other].

The second aspect of the present invention resides in a composition containing the polymerizable compound according to the first aspect.

The third aspect of the present invention resides in a polymer obtained by polymerizing the composition according to the second aspect.

The fourth aspect of the present invention resides in an optically anisotropic article including the polymer according to the third aspect.

The fifth aspect of the present invention resides in a liquid crystal display device including the optically anisotropic article according to the fourth aspect.

The sixth aspect of the present invention resides in an organic EL device including the optically anisotropic article according to the fourth aspect.

Advantageous Effects of Invention

The use of the polymerizable compounds according to the present invention makes it possible to produce optically anisotropic articles having excellent optical characteristics and to produce liquid crystal display devices having an improved viewing angle.

DESCRIPTION OF EMBODIMENTS

Hereinbelow, the present invention will be described based on some preferred embodiments without limiting the scope of the invention to such embodiments.

<<Polymerizable Compounds>>

The polymerizable compounds according to the first embodiment of the invention are represented by the following general formula (1-0):

[Chem. 2]

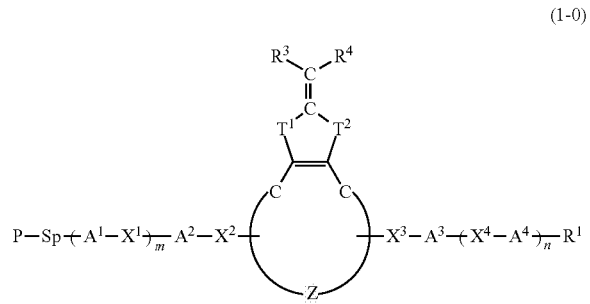

(1-0)

In the general formula (1-0), P is a polymerizable functional group, Sp is a spacer group or a single bond, $A^1$, $A^2$, $A^3$ and $A^4$ each independently represent a divalent alicyclic hydrocarbon group or aromatic hydrocarbon group, $X^1$, $X^2$, $X^3$ and $X^4$ each independently represent a divalent bonding group or a single bond, $R^1$ is an alkyl or alkoxy group having 1 to 12 carbon atoms, or "*-Sp-P" (* indicates $A^4$ or $A^3$), m and n are each independently an integer of 0 to 4 (wherein m+n is an integer of 2 or greater), Z in combination with C—C=C—C in the formula represents a naphthalene ring wherein the group including $X^2$ and the group including $X^3$ in the formula substitute for any two hydrogen atoms bonded to the naphthalene ring, $T^1$ and $T^2$ each independently represent —S—, —O—, —NR—, —CH$_2$—, —NH—, —C(=O)—, —S(=O)— or —C(=S)—, $R^2$ is a hydrogen atom, a halogen atom, an alkyl group having 1 to 6 carbon atoms, an alkoxy group having 1 to 6 carbon atoms, a cyano group, a nitro group or a hydroxyl group, $R^3$ and $R^4$ each independently represent a monovalent substituent or form a ring through Y which connects $R^3$ and $R^4$ together wherein when such a ring is formed, $R^3$ and $R^4$ each independently represent a group selected from the group consisting of —O—, —S—, —SO—, —SO$_2$—, —NR— (wherein R is a hydrogen atom or a monovalent substituent), =N—, =N(+)R— (wherein R is a hydrogen atom or a monovalent substituent), —C(=O)—, —C(=S)— and =CR— (wherein R is a hydrogen atom or a monovalent substituent), and Y represents 2 to 4 atoms selected from the group consisting of carbon atoms and Group XIV to Group XVI nonmetallic atoms, and in combination with $R^3$—C—$R^4$ in the formula forms a 5- to 7-membered ring which may be substituted with a monovalent substituent in place of any hydrogen atom bonded to the 5- to 7-membered ring, except when $T^1$ and $R^3$, and $T^2$ and $R^4$ are each the same as each other and when $T^1$ and $R^4$, and $T^2$ and $R^3$ are each the same as each other.

Preferably, the compounds represented by the general formula (1-0) have liquid crystallinity before being polymerized. That is, the compounds of the general formula (1-0) are preferably polymerizable liquid crystal compounds.

<Polymerizable Functional Groups: P>

The polymerizable functional group represented by P in the general formula (1-0) may be any group used in conventional polymerizable liquid crystal compounds without limitation. Examples include vinyl groups, p-stilbene groups, acrylic groups (acryloyl groups), methacrylic groups (methacryloyl groups), acryloyloxy groups, methacryloyloxy groups, carboxyl groups, methylcarbonyl groups, hydroxyl groups, amide groups, alkylamino groups having 1 to 4 carbon atoms, amino groups, epoxy groups, oxetanyl groups, aldehyde groups, isocyanate groups and thioisocyanate groups.

Some preferred polymerizable functional groups P are substituents selected from the group consisting of those substituents represented by the general formula (II-c), the general formula (II-d) and the general formula (II-e) below:

[Chem. 3]

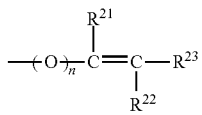

(II-c)

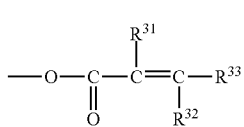

(II-d)

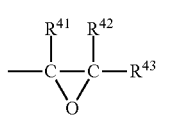

(II-e)

In the general formula (II-c), the general formula (II-d) and the general formula (II-e), $R^{21}$, $R^{22}$, $R^{23}$, $R^{32}$, $R^{33}$, $R^{41}$, $R^{42}$ and $R^{43}$ each independently represent a hydrogen atom, a halogen atom or an alkyl group having 1 to 5 carbon atoms, and n is 0 or 1. $R^{31}$ in the general formula (II-d) represents a hydrogen atom, a halogen atom, an alkyl group having 1 to 5 carbon atoms or a halogenated alkyl group having 1 to 5 carbon atoms.

The polymerizable functional group represented by any of the above general formulae is bonded to Sp in the general formula (1-0) via its left end.

The alkyl groups are preferably linear or branched alkyl groups, and are more preferably linear alkyl groups. Part or all of the hydrogen atoms bonded to the alkyl groups may be substituted by halogen atoms.

Of the polymerizable functional groups represented by the above general formulae, groups selected from the group consisting of those groups represented by the general formula (II-c) and the general formula (II-d) are preferable, and groups selected from the group consisting of those groups represented by the general formula (II-d) are more preferable from the point of view of enhancing the polymerizability and the storage stability.

Examples of the polymerizable functional groups represented by the general formula (II-c), the general formula (II-d) and the general formula (II-e) include reactive functional groups (P-1) to (P-8) illustrated below. Of these reactive functional groups, (P-1) or (P-2) is preferable, and (P-1) is more preferable from the point of view of enhancing the polymerizability and the storage stability. The polymerizable functional group represented by any of (P-1) to (P-8) is bonded to Sp in the general formula (1) via its right end.

[Chem. 4]

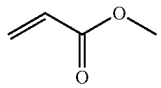
(P-1)

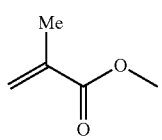
(P-2)

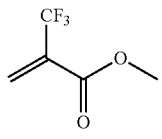
(P-3)

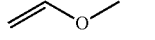
(P-5)

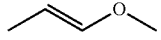
(P-6)

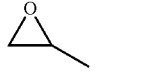
(P-7)

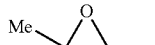
(P-8)

<Sp>

In the general formula (1-0), Sp is a spacer group or a single bond. The spacer group is a divalent bonding group which can connect the polymerizable functional group P to $A^1$ or $A^2$, and is preferably such a bonding group that does not cause a decrease in the liquid crystallinity of the compound represented by the general formula (1-0) (sometimes written as the compound (1-0) in the present specification).

For example, Sp is preferably a linear alkylene group having 1 to 20 carbon atoms, or is preferably a single bond. In the alkylene group, any one $CH_2$ group or any two or more $CH_2$ groups which are not adjacent to one another may be independently replaced by —O—, —S—, —NH—, —N(CH$_3$)—, —CO—, —COO—, —OCO—, —OCOO—, —SCO—, —COS—, —CH=CH— or —C≡C— in such a manner that no oxygen atoms, no sulfur atoms, or no oxygen and sulfur atoms are bonded directly to each other. To obtain an enhancement in liquid crystallinity, the number of carbon atoms in the alkylene group is preferably 2 to 10, more preferably 3 to 8, and still more preferably 3 to 6.

<Cyclic Groups: $A^1$, $A^z$, $A^3$ and $A^4$>

In the general formula (1-0), the cyclic groups $A^1$, $A^2$, $A^3$ and $A^4$ each independently represent a divalent alicyclic hydrocarbon group or aromatic hydrocarbon group. These cyclic groups may be aromatic heterocyclic groups.

Examples of the cyclic groups include 1,4-phenylene group, 1,4-cyclohexylene group, 1,4-cyclohexenyl group, tetrahydropyran-2,5-diyl group, 1,3-dioxane-2,5-diyl group, tetrahydrothiopyran-2,5-diyl group, 1,4-bicyclo(2,2,2)octylene group, decahydronaphthalene-2,6-diyl group, pyridine-2,5-diyl group, pyrimidine-2,5-diyl group, pyrazine-2,5-diyl group, 1,2,3,4-tetrahydronaphthalene-2,6-diyl group, 2,6-naphthylene group, phenanthrene-2,7-diyl group, 9,10-dihydrophenanthrene-2,7-diyl group, 1,2,3,4,4a,9,10a-octahydrophenanthrene 2,7-diyl group and fluorene 2,7-diyl group.

The 1,4-phenylene group, 1,4-cyclohexylene group, 1,2,3,4-tetrahydronaphthalene-2,6-diyl group, 2,6-naphthylene group, phenanthrene-2,7-diyl group, 9,10-dihydrophenanthrene-2,7-diyl group, 1,2,3,4,4a,9,10a-octahydrophenanthrene 2,7-diyl group and fluorene 2,7-diyl group may be substituted with F, Cl, CF$_3$, OCF$_3$, a cyano group, an alkyl group having 1 to 8 carbon atoms, an alkoxy group having 1 to 8 carbon atoms, an alkanoyl group having 1 to 8 carbon atoms, an alkanoyloxy group having 1 to 8 carbon atoms, an alkenyl group having 2 to 8 carbon atoms, an alkenyloxy group having 2 to 8 carbon atoms, an alkenoyl group having 2 to 8 carbon atoms or an alkenoyloxy group having 2 to 8 carbon atoms in place of one or more hydrogen atoms.

In the general formula (1-0), it is preferable that the cyclic groups $A^1$, $A^2$, $A^3$ and $A^4$ be each independently the 1,4-phenylene group or the 1,4-cyclohexylene group. With such cyclic groups, the polymerizable compound of the present embodiment achieves an enhanced liquid crystallinity and easily gives a polymer having an enhanced orientation.

<Bonding Groups or Single Bonds: $X^1$, $X^2$, $X^3$ and $X^4$>

In the general formula (1-0), $X^1$, $X^2$, $X^3$ and $X^4$ each independently represent a divalent bonding group or a single bond. Examples of the divalent bonding groups include —CH$_2$CH$_2$—, —CH=CH—, —C≡C—, —CH=CHCOO—, —OCO—CH=CH—, —(CH$_2$)$_u$—O—COO—, —(CH$_2$)$_u$—OCO—, —(CH$_2$)$_u$—COO—, —(CH$_2$)$_u$—O—, —O—COO—(CH$_2$)$_u$—, —OCO—(CH$_2$)$_u$—, —COO—(CH$_2$)$_u$— and —O—(CH$_2$)$_u$—, with —COO— and —OCO— being preferable.

Here, u indicates an integer of 0 to 2. When u is 0, —(CH$_2$)$_u$—COO— and —COO— (CH$_2$)$_u$— are each —COO—, and —(CH$_2$)$_u$—OCO— and —OCO—(CH$_2$)$_u$— are each —OCO—.

<m and n>

In the general formula (1-0), m and n are each independently an integer of 0 to 4, and m+n is an integer of 2 or greater.

To enhance the liquid crystallinity of the polymerizable compound in the present embodiment, m and n are preferably each independently 0 to 3, more preferably 0 to 2, and still more preferably 1 or 2. It is preferable that m and n be identical integers.

<Terminal Groups: $R^1$>

In the general formula (1-0), the terminal group $R^1$ is an alkyl group having 1 to 12 carbon atoms, an alkoxy group having 1 to 12 carbon atoms, or "*-Sp-P". Here, "*" indicates that the group is bonded to $A^4$ when n is an integer of 1 or greater or to $A^3$ when n is 0.

The Sp and the polymerizable functional group P in "*-Sp-P" are the same as described hereinabove. When there are two Sp's in the molecule, they may be the same as or different from each other and are preferably the same as each other. When there are two P's in the molecule, they may be the same as or different from each other and are preferably the same as each other.

The alkyl group may be a linear, branched or cyclic alkyl group, and is preferably a linear or branched alkyl group and more preferably a linear alkyl group. The number of carbon atoms in the alkyl group is more preferably 2 to 10, still more preferably 3 to 8, and further preferably 3 to 6.

The alkyl group constituting the alkoxy group may be similar to the above alkyl group. In the alkyl group constituting the alkoxy group, the number of carbon atoms is preferably 1 to 8, more preferably 1 to 6, and still more preferably 1 to 3.

In order to enhance the liquid crystallinity and orientation of the polymerizable compound according to the present embodiment and to enhance the optical characteristics of optically anisotropic articles such as retardation films including the polymerizable compound, it is preferable that the terminal group $R^1$ be "*-Sp-P". In this preferred embodiment, the two Sp's present in the molecule may be the same as or different from each other and are preferably the same as each other, and the two P's present in the molecule may be the same as or different from each other and are preferably the same as each other.

<Z>

In the general formula (1-0), Z represents a naphthalene ring in combination with C—C=C—C in the formula. The group including $X^2$ and the group including $X^3$ in the formula substitute for any two of the hydrogen atoms bonded to the naphthalene ring. Preferred examples of the polymerizable compounds represented by the general formula (1-0) include those polymerizable compounds represented by the following general formulae (1-1), (1-2) and (1-3):

[Chem. 5]

(1-1)

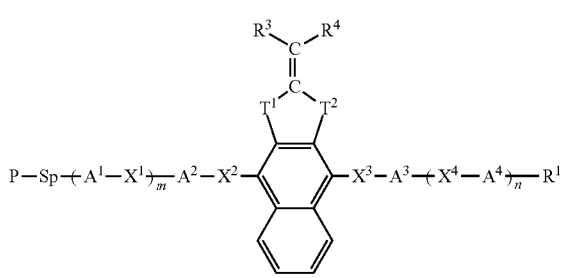

(1-2)

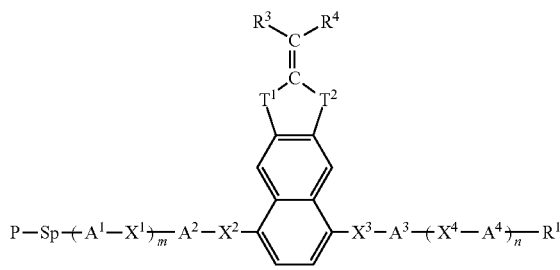

(1-3)

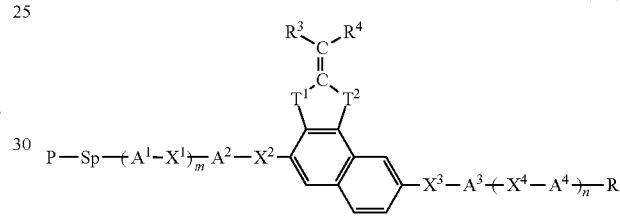

In the general formulae (1-1) to (1-3), P, Sp, $A^1$, $A^2$, $A^3$, $A^4$, $X^1$, $X^2$, $X^3$, $X^4$, $R^1$, m, n, $T^1$, $T^2$, $R^2$, $R^3$ and $R^4$ are the same as P, Sp, $A^1$, $A^2$, $A^3$, $A^4$, $X^1$, $X^2$, $X^3$, $X^4$, $R^1$, m, n, $T^1$, $T^2$, $R^2$, $R^3$ and $R^4$ in the formula (1-0).]

<$T^1$ and $T^2$>

In the general formula (1-0), $T_1$ and $T^2$ each independently represent —S—, —O—, —$NR^2$—, —$CH_2$—, —NH—, —C(=O)—, —S(=O)— or —C(=S)—. Here, $R^2$ is a hydrogen atom, a halogen atom, an alkyl group having 1 to 6 carbon atoms, an alkoxy group having 1 to 6 carbon atoms, a cyano group, a nitro group or a hydroxyl group. $T^1$ and $T^2$ may be the same as or different from each other. When $T^1$ and $T^2$ are each —$NR^2$—, the two $R^2$'s may be the same as or different from each other.

$T^1$ is preferably —O—, —$NR^2$— or —S—, more preferably —$NR^2$— or —S—, and still more preferably —S—.

$T^2$ is preferably —O—, —$NR^2$— or —S—, more preferably —$NR^2$— or —S—, and still more preferably —S—.

For the case in which $R^2$ is an alkyl group or an alkoxy group, examples of the alkyl groups and of the alkyl groups constituting the alkoxy groups as $R^2$ include methyl group, ethyl group, propyl group, isopropyl group, butyl group, isobutyl group, sec-butyl group, tert-butyl group, pentyl group and hexyl group. The number of carbon atoms in the alkyl group is preferably 1 to 4, more preferably 1 or 2, and still more preferably 1.

The halogen atom as $R^2$ is preferably a fluorine atom or a chlorine atom.

Preferred combinations of $T^1$ and $T^2$ are illustrated in the following general formulae (2-1) to (2-5):

[Chem. 6]

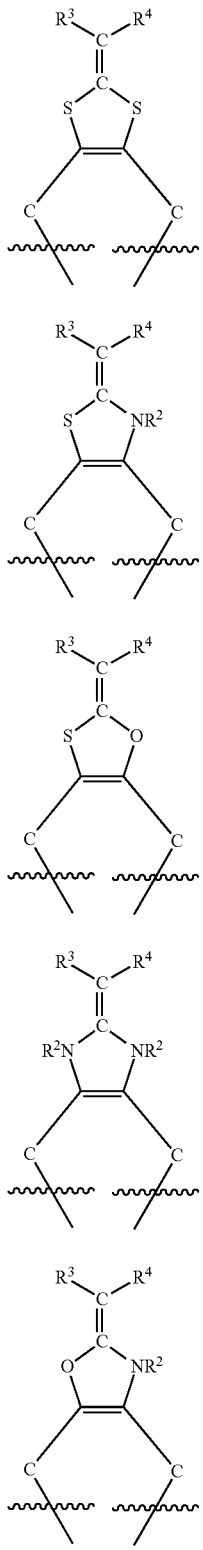

[In the formulae, the bonds intersected with a wiggly line are to Z in the general formula (1-0), and $R^3$ and $R^4$ are the same as $R^3$ and $R^4$ in the general formula (1-0).]

<$R^3$ and $R^4$>

In the general formula (1-0), $R^3$ and $R^4$ each independently represent a monovalent substituent or form a ring through Y which connects $R^3$ and $R^4$ together.

Examples of the monovalent substituents for each of $R^3$ and $R^4$ include alkyl groups, cycloalkyl groups, bicycloalkyl groups, alkenyl groups, cycloalkenyl groups, bicycloalkenyl groups, alkynyl groups, aryl groups, heterocyclic groups, cyano groups, carboxyl groups, hydroxyl groups, nitro groups, halogen atoms, alkoxy groups, aryloxy groups, silyloxy groups, heterocycloxy groups, acyloxy groups, carbamoyloxy groups, alkoxycarbonyloxy groups, aryloxycarbonyloxy groups, amino groups, acylamino groups, aminocarbonylamino groups, alkoxycarbonylamino groups, aryloxycarbonylamino groups, sulfamoylamino groups, alkyl- or arylsulfonylamino groups, mercapto groups, alkylthio groups, arylthio groups, heterocyclothio groups, sulfamoyl groups, sulfo groups, alkyl- or arylsulfinyl groups, alkyl- or arylsulfonyl groups, acyl groups, aryloxycarbonyl groups, alkoxycarbonyl groups, carbamoyl groups, aryl- or heterocycloazo groups, imide groups, phosphino groups, phosphinyl groups, phosphinyloxy groups, phosphinylamino groups and silyl groups.

Preferred monovalent substituents as $R^3$ and $R^4$ are monovalent organic groups containing at least one carbon atom. Specific examples include the alkyl groups described hereinabove, alkenyl groups, aryl groups, heterocyclic groups containing one or more carbon atoms, carboxyl groups, alkyl carboxylates (in which the alkyl groups preferably have 1 to 3 carbon atoms), alkoxy groups, aryloxy groups, acyloxy groups, cyano groups, and amino groups which have a substituent containing a carbon atom. Halogen atoms and hydroxyl groups are also usable.

More preferred monovalent substituents as $R^3$ and $R^4$ are cyano groups, alkyl carboxylates (in which the alkyl groups have, for example, 1 to 3 carbon atoms), alkyl groups and alkoxy groups. It is still more preferable that at least one of $R^3$ and $R^4$ be a cyano group or that $R^3$ or $R^4$ be an alkyl carboxylate.

The monovalent substituents as $R^3$ and $R^4$ will be described in detail below. In an embodiment, $R^3$ and $R^4$ each may lose a hydrogen atom to form a divalent group and such divalent groups may be bonded to each other to form a ring. This ring is formed without involving Y in the general formula (1-0).

<Details of Monovalent Substituents>

Examples of the alkyl groups include linear or branched, substituted or unsubstituted alkyl groups having 1 to 30 carbon atoms. Specific examples include methyl group, ethyl group, n-propyl group, isopropyl group, tert-butyl group, n-octyl group and 2-ethylhexyl group.

Examples of the cycloalkyl groups include substituted or unsubstituted cycloalkyl groups having 3 to 30 carbon atoms. Specific examples include cyclohexyl group, cyclopentyl group and 4-n-dodecylcyclohexyl group.

Examples of the bicycloalkyl groups include substituted or unsubstituted bicycloalkyl groups having 5 to 30 carbon atoms. Examples of the unsubstituted bicycloalkyl groups include monovalent groups resulting from the removal of one hydrogen atom from bicycloalkanes having 5 to 30 carbon atoms. Specific examples include bicyclo[1,2,2]heptan-2-yl group and bicyclo[2,2,2]octan-3-yl group.

Examples of the alkenyl groups include substituted or unsubstituted alkenyl groups having 2 to 30 carbon atoms. Specific examples include vinyl group and allyl group.

Examples of the cycloalkenyl groups include substituted or unsubstituted cycloalkenyl groups having 3 to 30 carbon atoms. Examples of the unsubstituted cycloalkenyl groups include monovalent groups resulting from the removal of one hydrogen atom from cycloalkenes having 3 to 30 carbon atoms. Specific examples include 2-cyclopenten-1-yl and 2-cyclohexen-1-yl group.

Examples of the bicycloalkenyl groups include substituted or unsubstituted bicycloalkenyl groups having 5 to 30 carbon atoms. Examples of the unsubstituted bicycloalkenyl groups include monovalent groups resulting from the removal of one hydrogen atom from bicycloalkenes having one double bond. Specific examples include bicyclo[2,2,1]hept-2-en-1-yl group and bicyclo[2,2,2]oct-2-en-4-yl group.

Examples of the alkynyl groups include substituted or unsubstituted alkynyl groups having 2 to 30 carbon atoms. Specific examples include ethynyl group and propargyl group.

Examples of the aryl groups include substituted or unsubstituted aryl groups having 6 to 30 carbon atoms. Specific examples include phenyl group, p-tolyl group and naphthyl group.

Examples of the heterocyclic groups include monovalent groups resulting from the removal of one hydrogen atom from 5- or 6-membered, substituted or unsubstituted, aromatic or nonaromatic heterocyclic compounds. More preferred groups are 5- or 6-membered aromatic heterocyclic groups having 3 to 30 carbon atoms. Specific examples include 2-furyl group, 2-thienyl group, 2-pyrimidinyl group and 2-benzothiazolyl group.

Examples of the alkoxy groups include substituted or unsubstituted alkoxy groups having 1 to 30 carbon atoms. Specific examples include methoxy group, ethoxy group, isopropoxy group, tert-butoxy group, n-octyloxy group and 2-methoxyethoxy group.

Examples of the aryloxy groups include substituted or unsubstituted aryloxy groups having 6 to 30 carbon atoms. Specific examples include phenoxy group, 2-methylphenoxy group, 4-tert-butylphenoxy group, 3-nitrophenoxy group and 2-tetradecanoylaminophenoxy group.

Examples of the silyloxy groups include those silyloxy groups having 3 to 20 carbon atoms. Specific examples include trimethylsilyloxy group and tert-butyldimethylsilyloxy group.

Examples of the heterocycloxy groups include substituted or unsubstituted heterocycloxy groups having 2 to 30 carbon atoms. Specific examples include 1-phenyltetrazol-5-oxy group and 2-tetrahydropyranyloxy group.

Examples of the acyloxy groups include formyloxy group, substituted or unsubstituted alkylcarbonyloxy groups having 2 to 30 carbon atoms, and substituted or unsubstituted arylcarbonyloxy groups having 6 to 30 carbon atoms. Specific examples include formyloxy group, acetyloxy group, pivaloyloxy group, stearoyloxy group, benzoyloxy group and p-methoxyphenylcarbonyloxy group.

Examples of the carbamoyloxy groups include substituted or unsubstituted carbamoyloxy groups having 1 to 30 carbon atoms. Specific examples include N,N-dimethylcarbamoyloxy group, N,N-diethylcarbamoyloxy group, morpholinocarbonyloxy group, N,N-di-n-octylaminocarbonyloxy group and N-n-octylcarbamoyloxy group.

Examples of the alkoxycarbonyloxy groups include substituted or unsubstituted alkoxycarbonyloxy groups having 2 to 30 carbon atoms. Specific examples include methoxycarbonyloxy group, ethoxycarbonyloxy group, tert-butoxycarbonyloxy group and n-octylcarbonyloxy group.

Examples of the aryloxycarbonyloxy groups include substituted or unsubstituted aryloxycarbonyloxy groups having 7 to 30 carbon atoms. Specific examples include phenoxycarbonyloxy group, p-methoxyphenoxycarbonyloxy group and p-n-hexadecyloxyphenoxycarbonyloxy group.

Examples of the amino groups include amino group, substituted or unsubstituted alkylamino groups having 1 to 30 carbon atoms, and substituted or unsubstituted anilino groups having 6 to 30 carbon atoms. Specific examples include amino group, methylamino group, dimethylamino group, anilino group, N-methyl-anilino group and diphenylamino group.

Examples of the acylamino groups include formylamino group, substituted or unsubstituted alkylcarbonylamino groups having 1 to 30 carbon atoms, and substituted or unsubstituted arylcarbonylamino groups having 6 to 30 carbon atoms. Specific examples include formylamino group, acetylamino group, pivaloylamino group, lauroylamino group and benzoylamino group.

Examples of the aminocarbonylamino groups include substituted or unsubstituted aminocarbonylamino groups having 1 to 30 carbon atoms. Specific examples include carbamoylamino group, N,N-dimethylaminocarbonylamino group, N,N-diethylaminocarbonylamino group and morpholinocarbonylamino group.

Examples of the alkoxycarbonylamino groups include substituted or unsubstituted alkoxycarbonylamino groups having 2 to 30 carbon atoms. Specific examples include methoxycarbonylamino group, ethoxycarbonylamino group, tert-butoxycarbonylamino group, n-octadecyloxycarbonylamino group and N-methyl-methoxycarbonylamino group.

Examples of the aryloxycarbonylamino groups include substituted or unsubstituted aryloxycarbonylamino groups having 7 to 30 carbon atoms. Specific examples include phenoxycarbonylamino group, p-chlorophenoxycarbonylamino group and m-n-octyloxyphenoxycarbonylamino group.

Examples of the sulfamoylamino groups include substituted or unsubstituted sulfamoylamino groups having 0 to 30 carbon atoms. Specific examples include sulfamoylamino group, N,N-dimethylaminosulfonylamino group and N-n-octylaminosulfonylamino group.

Examples of the alkyl- or arylsulfonylamino groups include substituted or unsubstituted alkylsulfonylamino groups having 1 to 30 carbon atoms, and substituted or unsubstituted arylsulfonylamino groups having 6 to 30 carbon atoms. Specific examples include methylsulfonylamino group, butylsulfonylamino group, phenylsulfonylamino group, 2,3,5-trichlorophenylsulfonylamino group and p-methylphenylsulfonylamino group.

Examples of the alkylthio groups include substituted or unsubstituted alkylthio groups having 1 to 30 carbon atoms. Specific examples include methylthio group, ethylthio group and n-hexadecylthio group.

Examples of the arylthio groups include substituted or unsubstituted arylthio groups having 6 to 30 carbon atoms. Specific examples include phenylthio group, p-chlorophenylthio group and m-methoxyphenylthio group.

Examples of the heterocyclothio groups include substituted or unsubstituted heterocyclothio groups having 2 to 30 carbon atoms. Specific examples include 2-benzothiazolylthio group and 1-phenyltetrazol-5-ylthio group.

Examples of the sulfamoyl groups include substituted or unsubstituted sulfamoyl groups having 0 to 30 carbon atoms. Specific examples include N-ethylsulfamoyl group, N-(3-dodecyloxypropyl)sulfamoyl group, N,N-dimethylsulfamoyl group, N-acetylsulfamoyl group, N-benzoylsulfamoyl group and N—(N'-phenylcarbamoyl)sulfamoyl group.

Examples of the alkyl- or arylsulfinyl groups include substituted or unsubstituted alkylsulfinyl groups having 1 to 30 carbon atoms, and substituted or unsubstituted arylsulfinyl groups having 6 to 30 carbon atoms. Specific examples include methylsulfinyl group, ethylsulfinyl group, phenylsulfinyl group and p-methylphenylsulfinyl group.

Examples of the alkyl- or arylsulfonyl groups include substituted or unsubstituted alkylsulfonyl groups having 1 to 30 carbon atoms, and substituted or unsubstituted arylsulfonyl groups having 6 to 30 carbon atoms. Specific examples include methylsulfonyl group, ethylsulfonyl group, phenylsulfonyl group and p-methylphenylsulfonyl group.

Examples of the acyl groups include formyl group, substituted or unsubstituted alkylcarbonyl groups having 2 to 30 carbon atoms, and substituted or unsubstituted arylcarbonyl groups having 7 to 30 carbon atoms. Specific examples include acetyl group and pivaloylbenzoyl group.

Examples of the aryloxycarbonyl groups include substituted or unsubstituted aryloxycarbonyl groups having 7 to 30 carbon atoms. Specific examples include phenoxycarbonyl group, o-chlorophenoxycarbonyl group, m-nitrophenoxycarbonyl group and p-tert-butylphenoxycarbonyl group.

Examples of the alkoxycarbonyl groups include substituted or unsubstituted alkoxycarbonyl groups having 2 to 30 carbon atoms. Specific examples include methoxycarbonyl group, ethoxycarbonyl group, tert-butoxycarbonyl group and n-octadecyloxycarbonyl group.

Examples of the carbamoyl groups include substituted or unsubstituted carbamoyl groups having 1 to 30 carbon atoms. Specific examples include carbamoyl group, N-methylcarbamoyl group, N,N-dimethylcarbamoyl group, N,N-di-n-octylcarbamoyl group and N-(methylsulfonyl)carbamoyl group.

Examples of the aryl- or heterocycloazo groups include substituted or unsubstituted arylazo groups having 6 to 30 carbon atoms, and substituted or unsubstituted heterocycloazo groups having 3 to 30 carbon atoms. Specific examples include phenylazo group, p-chlorophenylazo group and 5-ethylthio-1,3,4-thiadiazol-2-ylazo group.

Examples of the imide groups include N-succinimide group and N-phthalimide group.

Examples of the phosphino groups include substituted or unsubstituted phosphino groups having 2 to 30 carbon atoms. Specific examples include dimethylphosphino group, diphenylphosphino group and methylphenoxyphosphino group.

Examples of the phosphinyl groups include substituted or unsubstituted phosphinyl groups having 2 to 30 carbon atoms. Specific examples include phosphinyl group, dioctyloxyphosphinyl group and diethoxyphosphinyl group.

Examples of the phosphinyloxy groups include substituted or unsubstituted phosphinyloxy groups having 2 to 30 carbon atoms. Specific examples include diphenoxyphosphinyloxy group and dioctyloxyphosphinyloxy group.

Examples of the phosphinylamino groups include substituted or unsubstituted phosphinylamino groups having 2 to 30 carbon atoms. Specific examples include dimethoxyphosphinylamino group and dimethylaminophosphinylamino group.

Examples of the silyl groups include substituted or unsubstituted silyl groups having 3 to 30 carbon atoms. Specific examples include trimethylsilyl group, tert-butyldimethylsilyl group and phenyldimethylsilyl group.

Examples of the halogen atoms include fluorine atom, chlorine atom, bromine atom and iodine atom.

Examples further include groups resulting from the substitution of the monovalent substituents described above with any of the monovalent substituents described above in place of hydrogen atoms. Specific examples include alkylcarbonylaminosulfonyl groups, arylcarbonylaminosulfonyl groups, alkylsulfonylaminocarbonyl groups and arylsulfonylaminocarbonyl groups. More specific examples include methylsulfonylaminocarbonyl group, p-methylphenylsulfonylaminocarbonyl group, acetylaminosulfonyl group and benzoylaminosulfonyl group.

The monovalent substituents described above may be used in any combination with Z, the aforementioned preferred combinations of $T^1$ and $T^2$, and preferred combinations of the group including $X^2$ and the group including $X^3$.

<Formation of Ring with Y>

When $R^3$ and $R^4$ in the general formula (1-0) form a ring through Y, the compound is represented by the following general formula (1-0-0):

[Chem. 7]

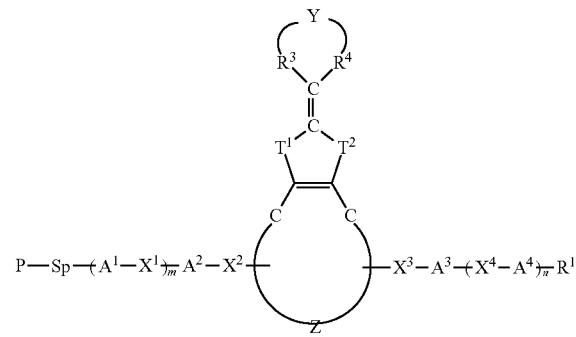

(1-0-0)

In this case, $R^3$ and $R^4$ each independently represent a group selected from the group consisting of —O—, —S—, —SO—, —SO$_2$—, —NR— (wherein R is a hydrogen atom or a monovalent substituent), =N—, =N(+)R— (wherein R is a hydrogen atom or a monovalent substituent), —C(=O)—, —C(=S)— and =CR— (wherein R is a hydrogen atom or a monovalent substituent). For the case in which R is a monovalent substituent, examples of the monovalent substituents include those monovalent substituents described hereinabove for $R^3$ and $R^4$.

Y represents 2 to 4 atoms selected from the group consisting of carbon atoms and Group XIV to Group XVI nonmetallic atoms, and forms a 5- to 7-membered ring (hereinafter, also written as the ring Y) in combination with $R^3$—C—$R^4$ in the general formula (1-0-0). When the atoms constituting the ring Y have substitutable hydrogen atoms, such hydrogen atoms may be substituted by substituents $R^Y$. Examples of $R^Y$ include those monovalent substituents described hereinabove for $R^3$ and $R^4$.

Preferred examples of the structure of the ring Y will be illustrated below. In the structural formulae, the bonds =C intersected with a wiggly line are to the 5-membered ring including $T^1$ and $T^2$.

[Chem. 8]
(Y1) 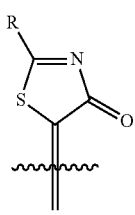
(Y2) 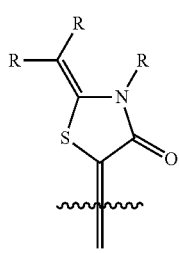
(Y3) 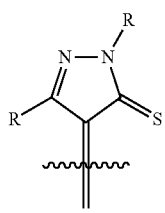
(Y4) 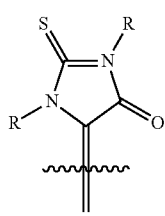
(Y5) 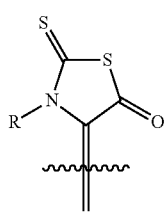
(Y6) 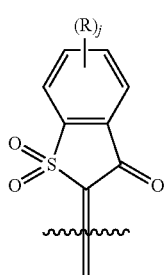
(Y7) 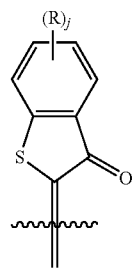
(Y8) 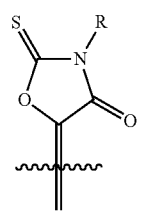
(Y9) 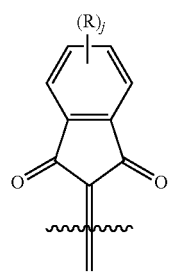
(Y10) 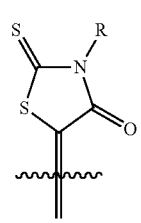
(Y11) 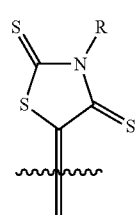
(Y12) 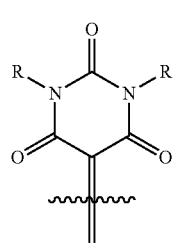

(Y13) 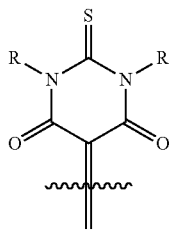

(Y14) 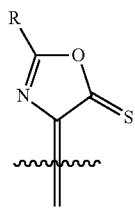

(Y15) 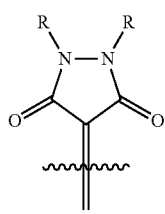

(Y16) 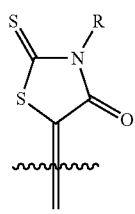

(Y17) 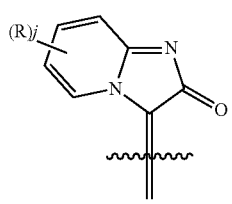

(Y18) 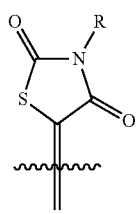

(Y19) 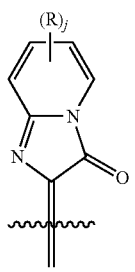

(Y20) 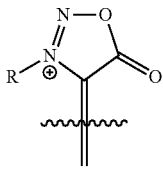

(Y21) 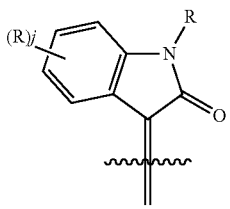

(Y22) 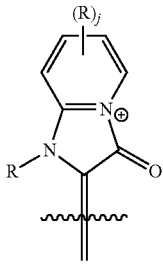

(Y23) 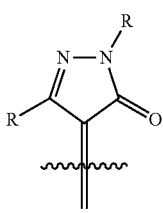

(Y24) 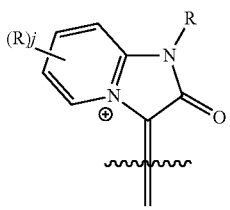

In the formulae (Y-1) to (Y-24), R is a hydrogen atom or a monovalent substituent. Examples of the monovalent substituents include those monovalent substituents described hereinabove for $R^3$ and $R^4$. When the structure contains a plurality of R's, they may be the same as or different from one another. In the formulae (Y-1) to (Y-24), j is an integer of 0 to 4 and the bonds =C intersected with a wiggly line are to the 5-membered ring including $T^1$ and $T^2$ in the general formula (1-0-0).

Examples of R in the formula (Y-1) include —N(Ph)$_2$, in which Ph represents a phenyl group. Referring to the formula (Y-2), examples of R bonded to N include alkyl groups having about 1 to 3 carbon atoms such as ethyl group, and examples of two R's bonded to C= include CN. Referring to the formula (Y-3), examples of R bonded to N include substituted or unsubstituted phenyl groups, and examples of R bonded to C include alkyl groups having about 1 to 3 carbon atoms such as methyl group. Referring to the formula (Y-4), examples of two R's bonded to N's include alkyl groups having about 1 to 3 carbon atoms such as ethyl group, and substituted or unsubstituted phenyl groups.

Examples of R bonded to N in the formulae (Y-5) and (Y-8) include alkyl groups having about 1 to 3 carbon atoms such as ethyl group. Examples of R bonded to N in the formula (Y-10) include substituted or unsubstituted phenyl groups. Examples of R bonded to N in the formulae (Y-11) to (Y-13) include alkyl groups having about 1 to 3 carbon atoms such as ethyl group. Examples of R bonded to C in the formula (Y-14) include substituted or unsubstituted phenyl groups. Examples of two R's bonded to N's in the formula (Y-15) include alkyl groups having about 1 to 3 carbon atoms such as methyl group, and substituted or unsubstituted phenyl groups.

Examples of R bonded to N in the formula (Y-16) include alkyl groups having about 1 to 3 carbon atoms such as ethyl group. Examples of R bonded to N in the formulae (Y-18) and (Y-20) include substituted or unsubstituted phenyl groups. Examples of R bonded to N in the formulae (Y-21) and (Y-22) include alkyl groups having about 1 to 3 carbon atoms such as methyl group and ethyl group. Referring to the formula (Y-23), examples of R bonded to N include substituted or unsubstituted phenyl groups, and examples of R bonded to C include hydrogen atom, —OH and ester groups (—COOR: R is an alkyl group having about 1 to 3 carbon atoms such as ethyl group). Examples of R bonded to N in the formula (Y-24) include alkyl groups having about 1 to 3 carbon atoms such as methyl group.

Of the rings Y illustrated above, those of the formula (Y-1), the formula (Y-5), the formula (Y-8), the formula (Y-9), the formula (Y-12), the formula (Y-13), the formula (Y-15), the formula (Y-21) and the formula (Y-23) are preferable, and those of the formula (Y-5), the formula (Y-9), the formula (Y-13), the formula (Y-15) and the formula (Y-23) are more preferable. The following structural formulae illustrate five examples of the combinations of the rings Y with the general formula (2-1) described hereinabove.

[Chem. 9]

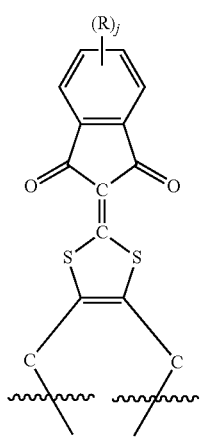
(2-1-1)

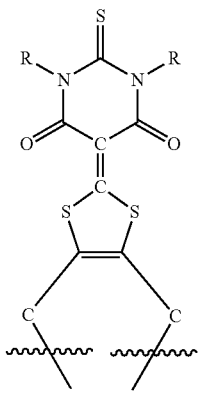
(2-1-2)

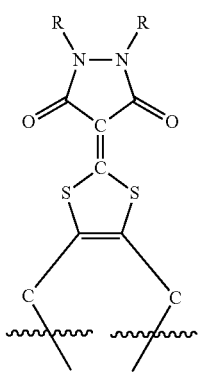
(2-1-3)

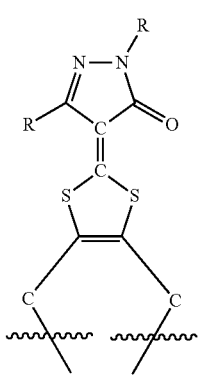
(2-1-4)

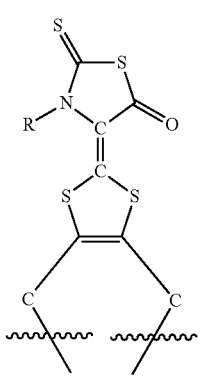
(2-1-5)

In the formulae (2-1-1) to (2-1-5), S represents a sulfur atom and the other characters are as defined with respect to the corresponding formulae (Y-9), (Y-13), (Y-15), (Y-23) and (Y-5).

The rings Y described above may be used in any combination with Z described hereinabove, the aforementioned preferred combinations of $T^1$ and $T^2$, and preferred combinations of the group including $X^2$ and the group including $X^3$.

One of the reasons as to why the polymerizable compounds represented by the general formula (1-0) have a small or reverse wavelength dispersion of birefringence (Δn) is probably because the naphthalene ring represented by Z has a large dipole moment in the lateral direction. In an optically anisotropic article such as a retardation film, the molecules of the polymerizable compound represented by the general formula (1-0) are oriented so that the longer molecular axes defined by the group including $X^2$, the naphthalene ring and the group including $X^3$ are aligned with respect to one another. With this configuration, the compound comes to exhibit an anisotropic refractive index. The small or reverse birefringence is probably ascribed to this fact and to the fact that the dipole moments are directed to the lateral direction of the longer molecular axes.

The following illustrate specific examples of the polymerizable compounds represented by the general formula (1-0) without limiting the scope of the invention to such examples.

[Chem. 10]

(1-1-1)

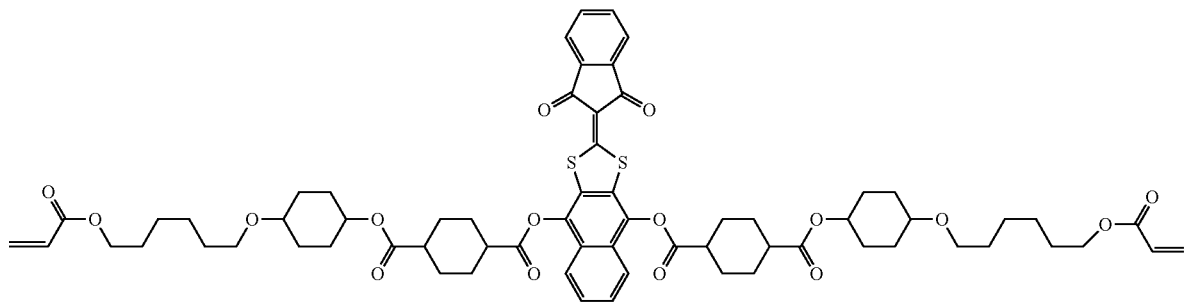

(1-1-2)

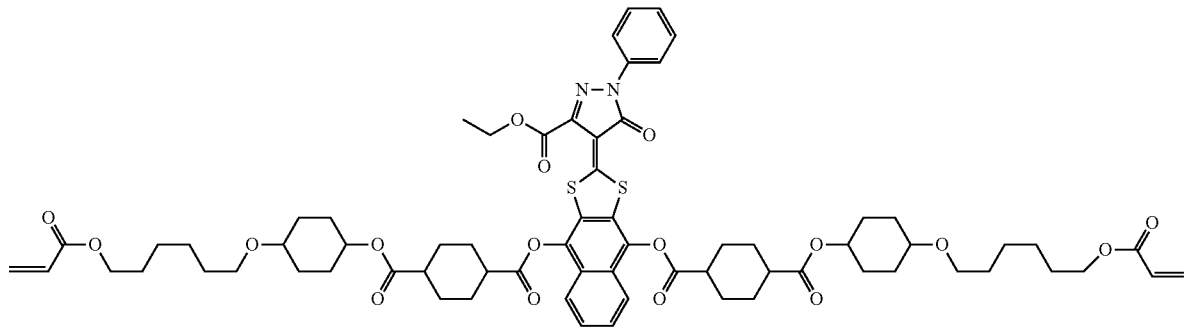

(1-1-3)

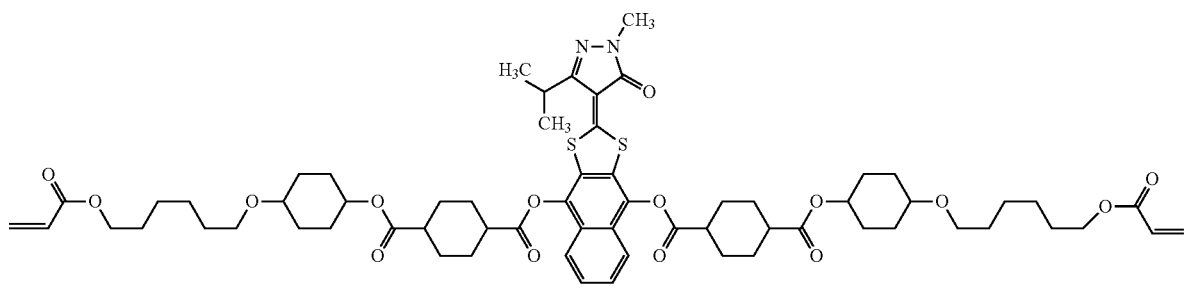

(1-1-4)

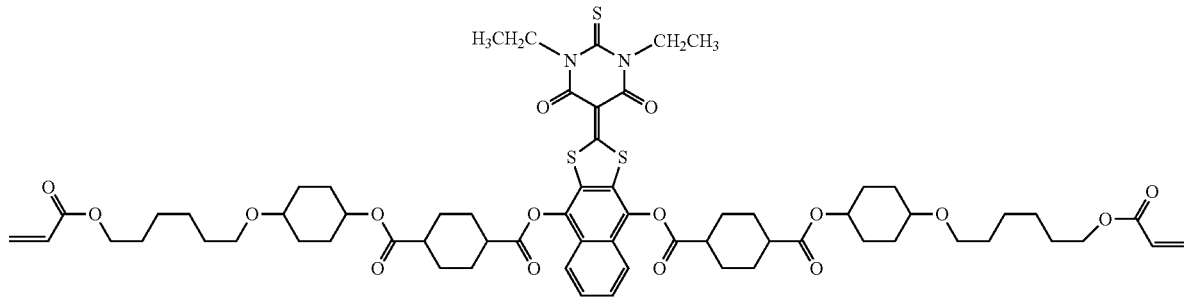

[Chem. 11]
(1-1-5)
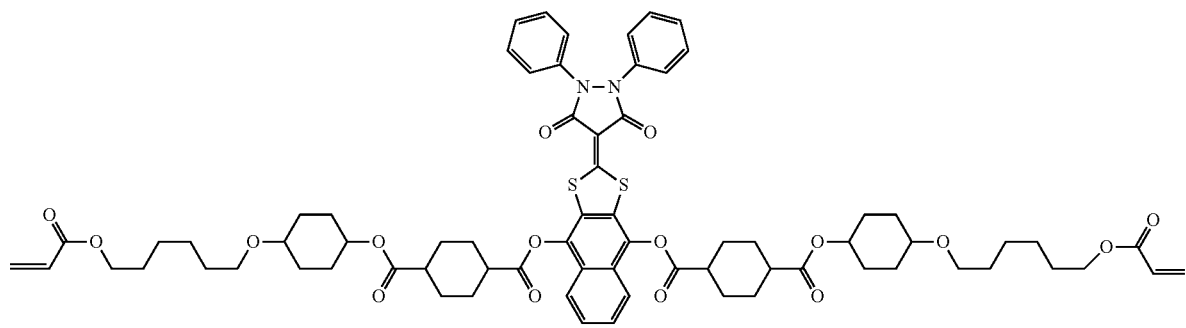
(1-1-6)
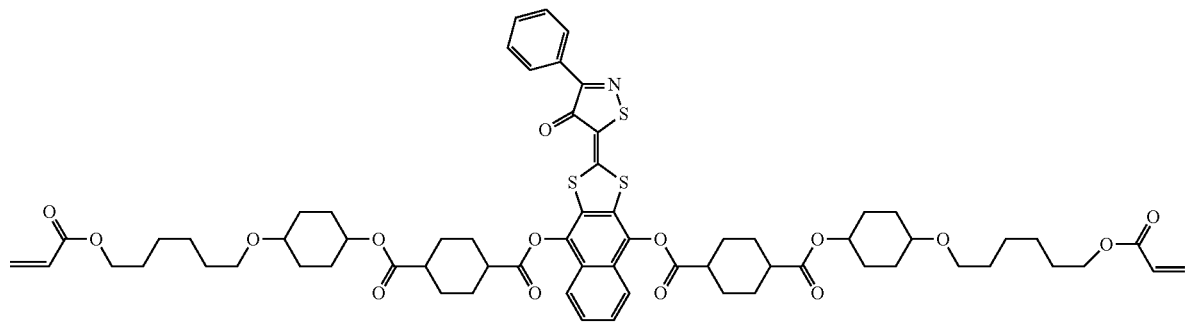
(1-1-7)
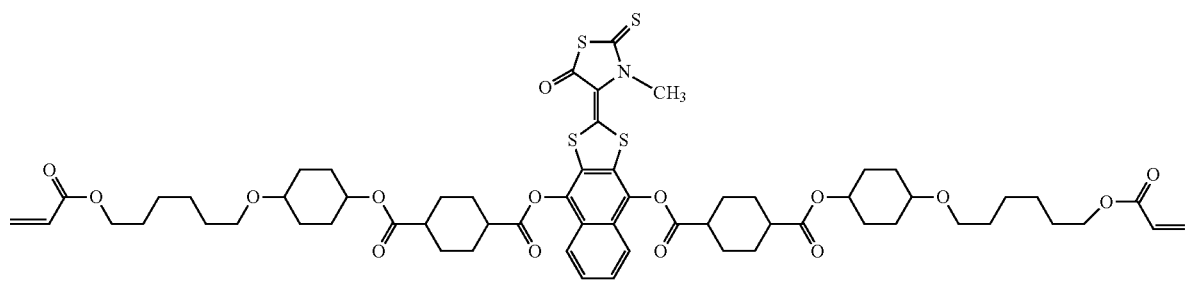
(1-1-8)
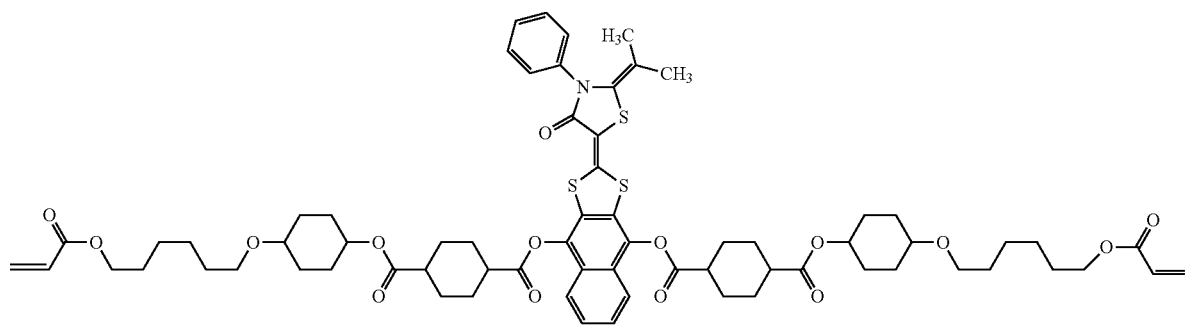

[Chem. 12]
(1-1-9)
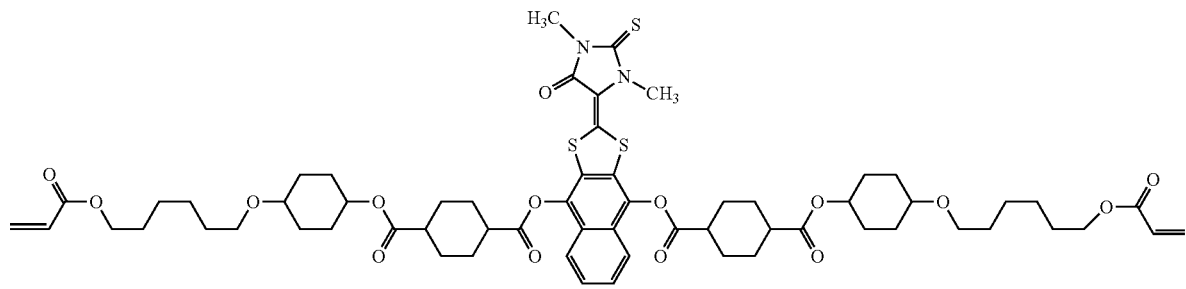
(1-1-10)
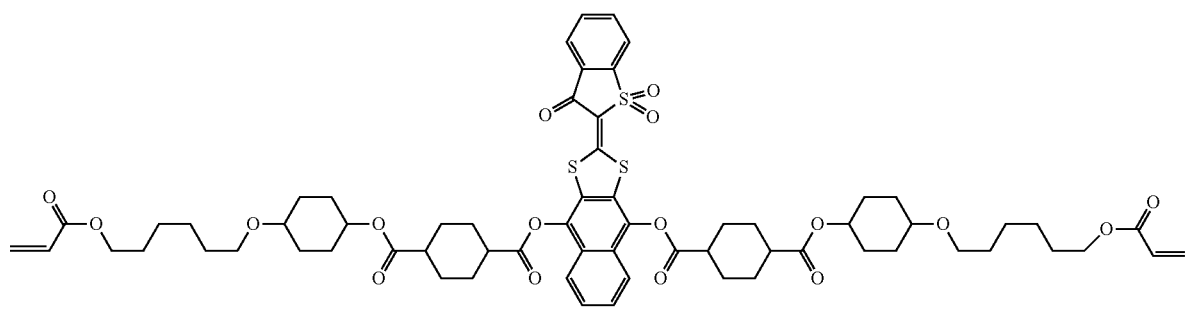
(1-1-11)
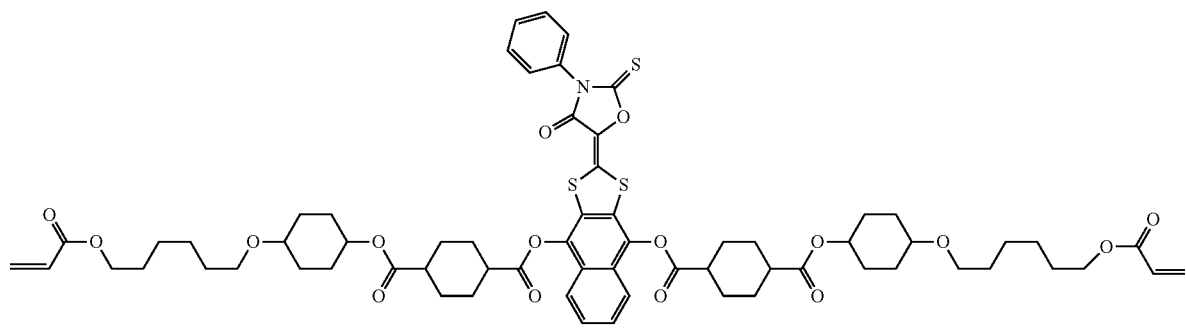
(1-1-12)
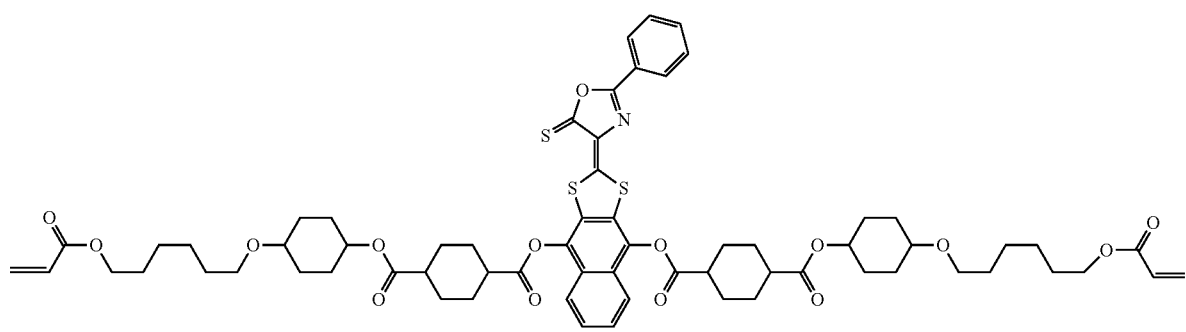

[Chem. 13]
(1-1-13)
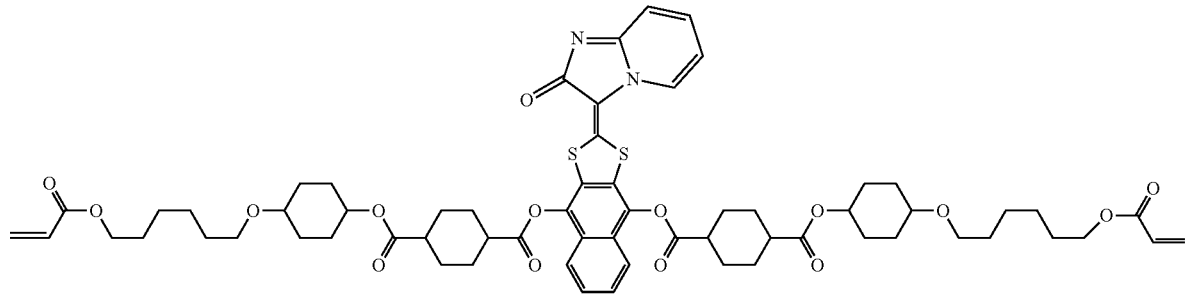
(1-1-14)
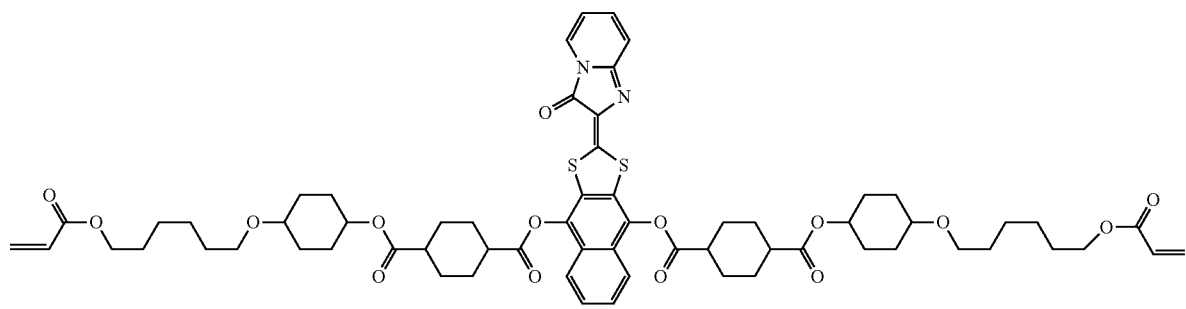
[Chem. 14]
(1-1-15)
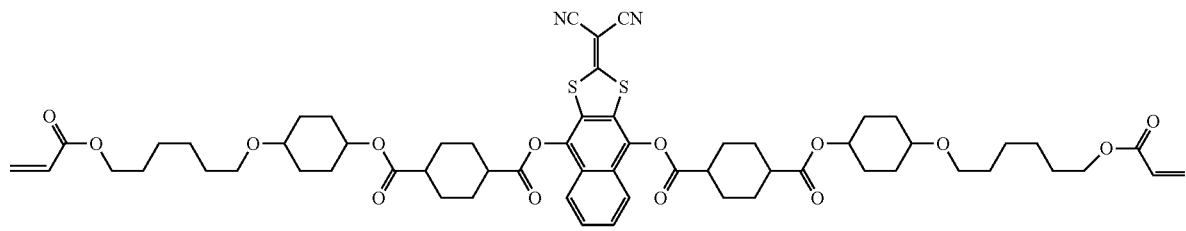
(1-1-16)
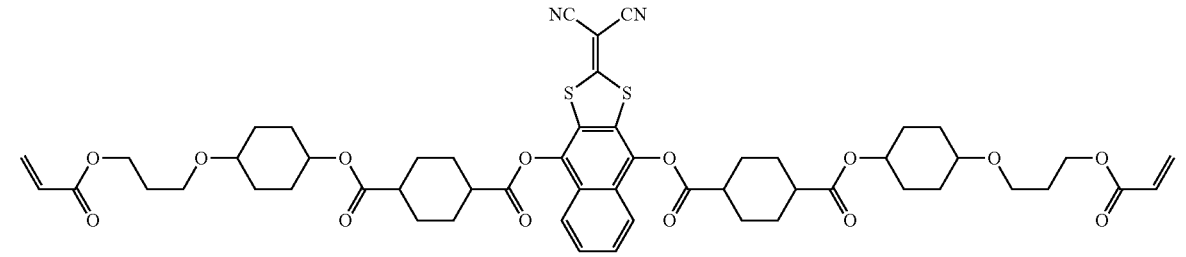
(1-1-17)
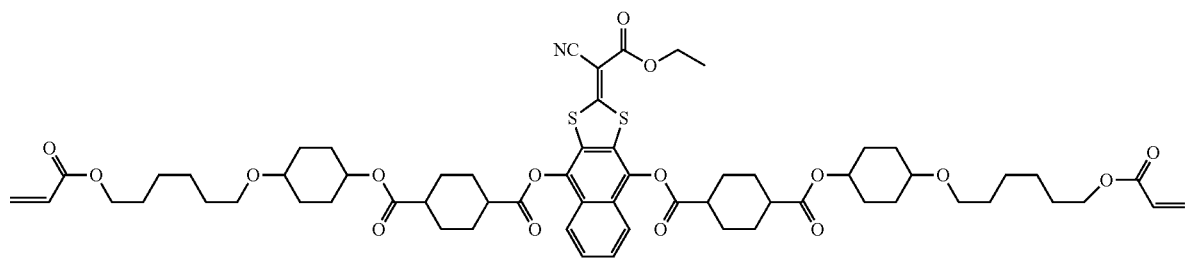

<<Compositions>>

The compositions of the second embodiment according to the present invention include the polymerizable compounds of the first embodiment. In the present embodiment, the composition may contain a single kind of the polymerizable compound represented by the general formula (1-0) or may contain two or more kinds of such compounds. It is usually preferable that the composition contain 1 to 4 kinds of the compounds, more preferably 1 to 3 kinds of the compounds, and still more preferably 1 or 2 kinds of the compounds.

The composition of the present embodiment may contain other known polymerizable compounds in addition to the polymerizable compounds of the first embodiment. Examples of such known polymerizable compounds include those polymerizable compounds represented by the general formulae (A1) to (A24) below.

[Chem. 15]

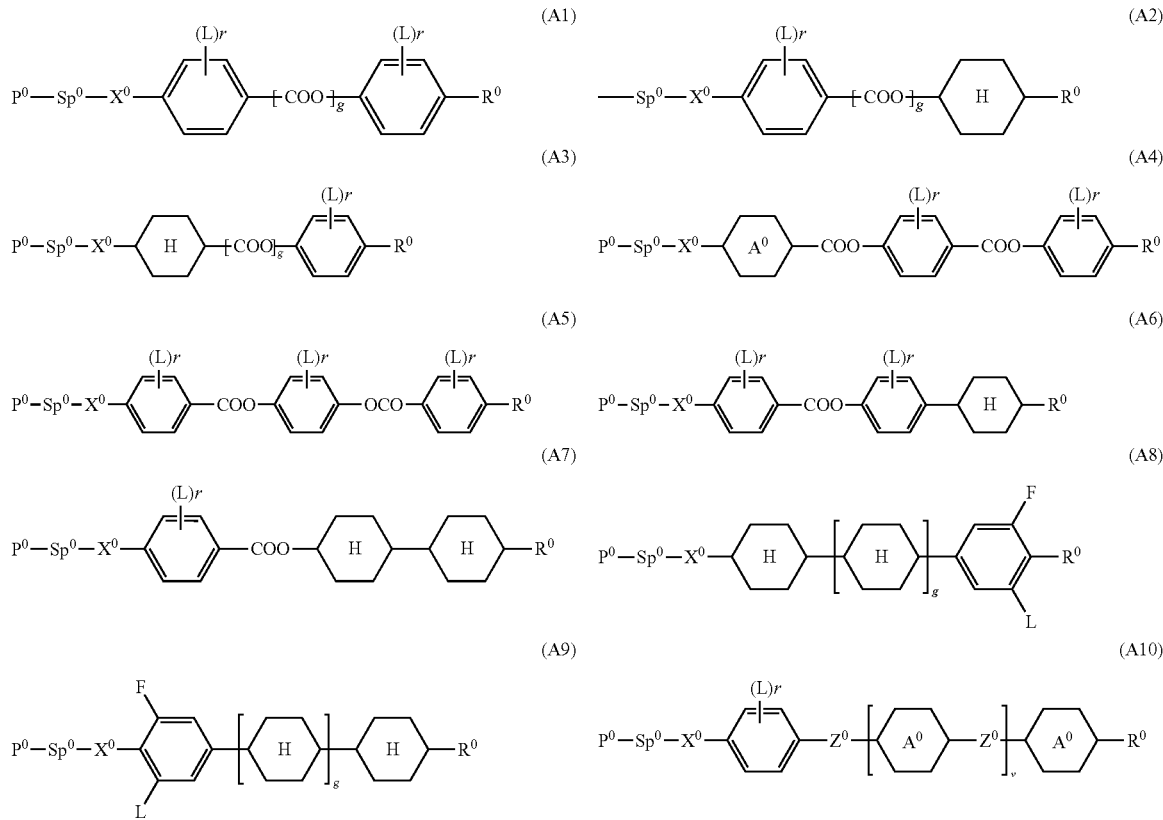

[Chem. 16]

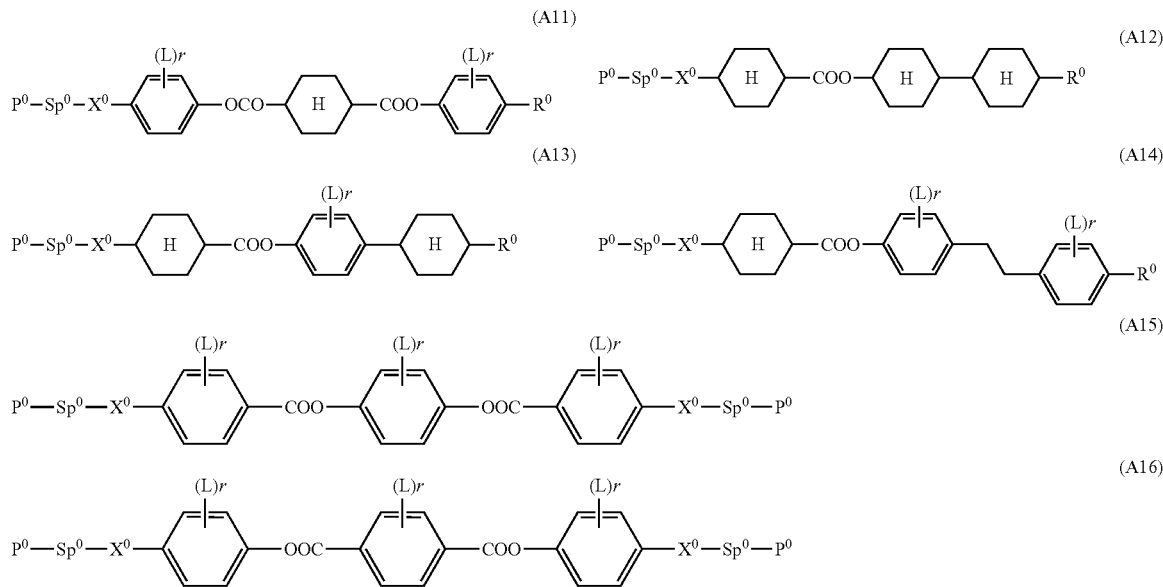

-continued

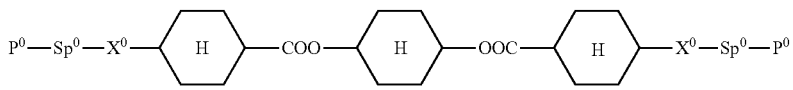
(A17)

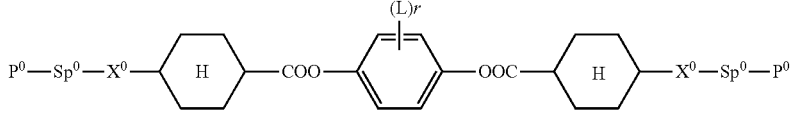
(A18)

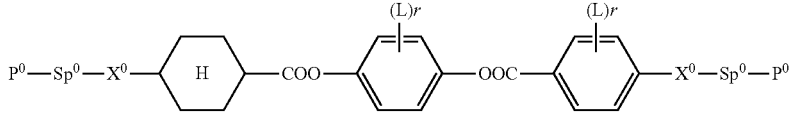
(A19)

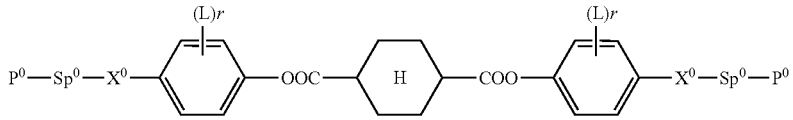
(A20)

[Chem. 17]

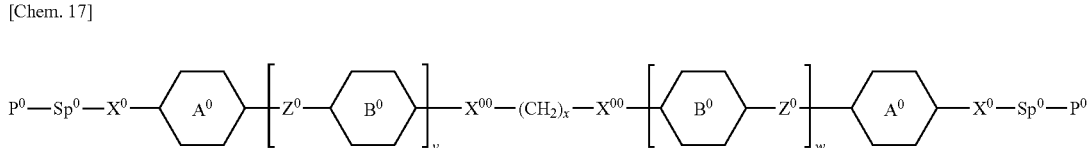
(A21)

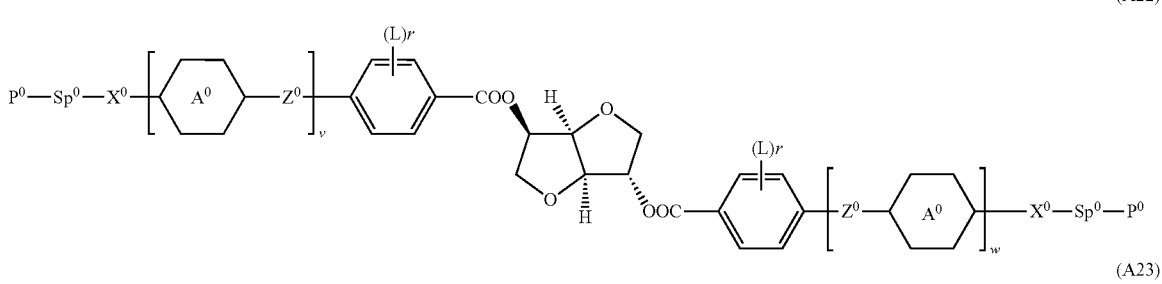
(A22)

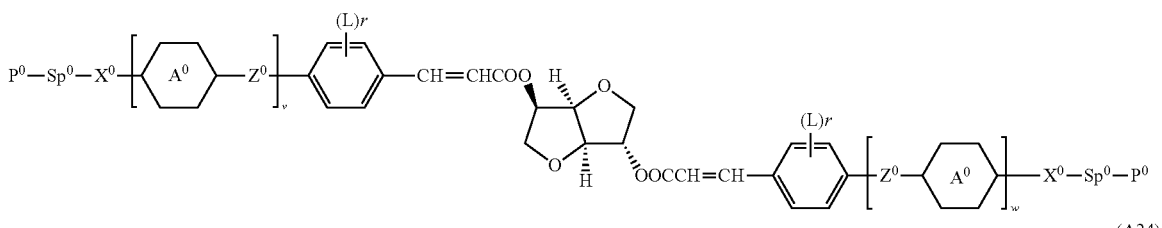
(A23)

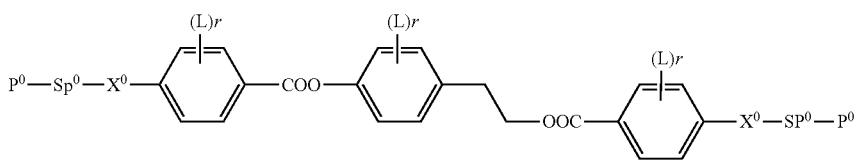
(A24)

In the general formulae (A1) to (A24), $P^0$ independently at each occurrence represents a polymerizable group having one of the definitions of P described hereinabove, and preferably represents an acrylic, methacrylic, oxetane, 3-ethyloxetane, epoxy, vinyloxy or styrene group;

$Sp^0$ represents a spacer group having one of the definitions of Sp described hereinabove, or a single bond;

$X^0$ represents —O—, —S—, —CO—, —COO—, —OCO—, —O—COO—, —CO—NR$^0$—, —NR$^0$—CO—, —NR$^0$—CO—NR—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond;

$Sp^0$-$X^0$ is preferably selected from —(CH$_2$)$_{p1}$—, —(CH$_2$)$_{p1}$—O—, —(CH$_2$)$_{p1}$—CO—O— and —(CH$_2$)$_{p1}$—O—CO—O— wherein p1 is an integer of 1 to 12 and these groups are bonded to the adjacent rings via the oxygen atom when present;

$A^0$ and $B^0$ independently at each occurrence represent 1,4-phenylene (which may be substituted with one, two, three or four groups L) or trans-1,4-cyclohexylene;

H represents trans-1,4-cyclohexylene;

$Z^o$ independently at each occurrence represents —COO—, —OCO—, —CH$_2$CH$_2$—, —C≡C—, —CH=CH—, —CH=CH—COO—, —OCO—CH=CH— or a single bond;

$R^o$ is an alkyl, alkoxy, thioalkyl, alkylcarbonyl, alkoxycarbonyl, alkylcarbonyloxy or alkoxycarbonyloxy group (which may be fluorinated) having 1 to 20, preferably 1 to 15 carbon atoms, or represents $Y^o$ or P-Sp$^o$-X$^o$—;

$Y^o$ represents F, Cl, CN, NO$_2$, OCH$_3$, OCN, SCN, SF$_5$, an optionally fluorinated alkylcarbonyl, alkoxycarbonyl, alkylcarbonyloxy or alkoxycarbonyloxy group having 1 to 4 carbon atoms, or a monofluorinated, oligofluorinated or polyfluorinated alkyl or alkoxy group having 1 to 4 carbon atoms;

$X^{oo}$ represents —O—, —S—, —CO—, —COO—, —OCO—, —O—COO—, —CO—NR$^{o1}$—, —NR$^{o1}$—CO—, —NR$^{o1}$—CO—NR$^{o1}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^{o1}$—, —CF=CF—, —C≡C—, —CH=CH—COO—, —OCO—CH=CH— or a single bond;

$R^{o1}$ is hydrogen or an alkyl having 1 to 12 carbon atoms;

L, which may be the same or different when plural, represents F, Cl, CN, SCN, SF$_5$, a linear or branched and optionally monofluorinated or polyfluorinated alkyl, alkoxy, alkenyl, alkynyl, alkylcarbonyl, alkoxycarbonyl, alkylcarbonyloxy or alkoxycarbonyloxy group having 1 to 12 carbon atoms (with the proviso that those groups other than the alkyl and the alkoxy have at least 2 carbon atoms, and branched groups have at least 3 carbon atoms), or an optionally halogenated alkyl, alkoxy, alkylcarbonyl, alkoxycarbonyl, alkylcarbonyloxy or alkoxycarbonyloxy group having 1 to 5 carbon atoms;

r is 0, 1, 2, 3 or 4;

g is 0 or 1;

v and w are each independently 0, 1 or 2; and the benzene rings and the naphthalene rings may be additionally substituted with one or more groups L which may be the same as or different from one another.

In the general formulae (A1) to (A24), "—OOC—" represents "—O—C(=O)—" and is the same as "—OCO—"

The total content of the polymerizable compound(s) represented by the general formula (1-0) is preferably 10 to 100 parts by weight, more preferably 30 to 100 parts by weight, and still more preferably 50 to 100 parts by weight with respect to the total weight of all the polymerizable compounds in the composition of the present embodiment taken as 100 parts by weight.

The composition of the present embodiment preferably includes a bifunctional compound having two polymerizable functional groups in the molecule. The incorporation of such a bifunctional compound imparts excellent properties such as orientation and optical characteristics in the use as polymer substrates and stacks including such substrates.

Specific examples of such uses include optically anisotropic articles in the field of liquid crystal displays such as retardation films, patterned retardation films and homogeneously aligned (horizontally aligned) liquid crystal films.

The substrates to which a solution containing the composition of the present embodiment is applied may be any of common substrates used in liquid crystal devices, displays, optical components and optical films and are not particularly limited as long as the materials have heat resistance enough to withstand heat applied during drying after the application of the composition of the present embodiment or during the manufacturing of liquid crystal devices. Examples of such substrates include glass substrates, metal substrates, ceramic substrates and organic materials such as polymer substrates. In particular, polymer substrates are advantageous in that they can be fabricated from roll to roll and are handled easily compared to other materials such as glass substrates. Further, substrates made of polymer compounds (polymer substrates) have excellent affinity for the polymerizable compounds of the first embodiment and therefore a solution containing the polymerizable compound can be applied and dried on a polymer substrate so as to easily achieve excellent orientation. From this point of view, the polymerizable compounds of the present embodiment are suitably used in applications in which they are stacked onto polymer substrates.

Examples of the polymer compounds for forming such preferred polymer substrates include cellulose derivatives, polyolefins, polyesters, polyethylene terephthalates, polycarbonates, polyacrylates, polyarylates, polyethersulfones, polyimides, polyphenylene sulfides, polyphenylene ethers, nylons and polystyrenes. Cycloolefin polymers, triacetyl celluloses and polymethyl methacrylate resins are particularly preferable.

An alignment treatment may be performed on the substrate to facilitate the orientation of the polymerizable compound when the composition of the present embodiment is applied and dried. The alignment treatment may be direct rubbing on the substrate or may be the application of an alignment film used in general liquid crystal devices followed by rubbing. A known technique involving an optical alignment film is particularly preferable. The use of such an optical alignment film makes it possible to fabricate a patterned retardation film.

<Organic Solvents>

The composition of the present embodiment may include any type of an organic solvent without limitation as long as the solvent can dissolve the polymerizable compounds represented by the general formula (1-0). Preferred solvents are those solvents which are volatilized at a temperature of not more than 100° C. to allow the composition to dry and which do not corrode the substrate used. Examples of such solvents include aromatic hydrocarbons such as toluene, xylene, cumene and mesitylene, ester solvents such as methyl acetate, ethyl acetate, propyl acetate and butyl acetate, ketone solvents such as methyl ethyl ketone, methyl isobutyl ketone, cyclohexanone and cyclopentanone, ether solvents such as tetrahydrofuran, 1,2-dimethoxyethane and anisole, amide solvents such as N,N-dimethylformamide and N-methyl-2-pyrrolidone, propylene glycol monomethyl ether acetate, diethylene glycol monomethyl ether acetate, γ-butyrolactone, chlorobenzene and chloroform. These organic solvents may be used singly, or two or more may be used in combination.

Of the organic solvents described above, chloroform, toluene, ethyl acetate, methyl ethyl ketone, methyl isobutyl ketone, cyclohexanone, cyclopentanone, propylene glycol monomethyl ether acetate and N-methyl-2-pyrrolidone are more preferable because these solvents exhibit excellent solvency for the polymerizable compounds of the general formula (1-0), allow the composition to give a polymer film having excellent orientation, and are easily dried at 100° C. or below.

The content of the organic solvent may be controlled appropriately to ensure that the composition can be easily applied onto the substrate and is, for example, preferably 40 to 90 wt %, and more preferably 50 to 80 wt % relative to the total weight of the composition of the present embodiment.

<Polymerization Initiators>>

The composition of the present embodiment preferably includes at least one or more polymerization initiators.

Polymerization initiators are compounds useful to efficiently polymerize the polymerizable compounds of the first embodiment. Preferred polymerization initiators are photopolymerization initiators. Specifically, preferred compounds are IRGACURE 651, IRGACURE 184, IRGACURE 907, IRGACURE 127, IRGACURE 369, IRGACURE 379, IRGACURE 819, IRGACURE OXE01, IRGACURE OXE02, LUCIRIN TPO and DAROCUR 1173 manufactured by BASF, ESACURE 1001M, ESACURE KIP150, SPEEDCURE BEM, SPEEDCURE BMS and SPEEDCURE PBZ manufactured by LAMBSON, and benzophenone.

These polymerization initiators may be used singly, or two or more may be used in combination. Further, other additives such as sensitizers may be added.

For example, the content of the polymerization initiator is preferably 0.1 to 10 wt %, more preferably 1.0 to 7.0 wt %, and still more preferably 3.0 to 6.0 wt % relative to the total weight of the solids in the composition of the present embodiment.

<Surfactants and Other Components>

The composition of the present embodiment preferably includes a surfactant or a compound which has repeating units represented by the general formula (VI) below and has a weight average molecular weight of not less than 100.

$$+CR^{11}R^{12}-CR^{13}R^{14}+ \qquad (VI)$$

[In the formula, $R^{11}$, $R^{12}$, $R^{13}$ and $R^{14}$ each independently represent a hydrogen atom, a halogen atom or a hydrocarbon group having 1 to 20 carbon atoms, and the hydrocarbon group may be substituted with a halogen atom in place of one or more hydrogen atoms.]

The surfactants and the compounds represented by the general formula (VI) provide an effect of reducing the tilt angle of the liquid crystal compound at the interface with air. Examples of the surfactants include alkyl carboxylate salts, alkyl phosphate salts, alkyl sulfonate salts, fluoroalkyl carboxylate salts, fluoroalkyl phosphate salts, fluoroalkyl sulfonate salts, polyoxyethylene derivatives, fluoroalkyl ethylene oxide derivatives, polyethylene glycol derivatives, alkyl ammonium salts, fluoroalkyl ammonium salts and silicone derivatives. Of these, fluorine-containing surfactants and silicone derivatives are particularly preferable.

Specific examples include "MEGAFAC F-110", "MEGAFAC F-113", "MEGAFAC F-120", "MEGAFAC F-812", "MEGAFAC F-142D", "MEGAFAC F-144D", "MEGAFAC F-150", "MEGAFAC F-171", "MEGAFAC F-173", "MEGAFAC F-177", "MEGAFAC F-183", "MEGAFAC F-195", "MEGAFAC F-824", "MEGAFAC F-833", "MEGAFAC F-114", "MEGAFAC F-410", "MEGAFAC F-493", "MEGAFAC F-494", "MEGAFAC F-443", "MEGAFAC F-444", "MEGAFAC F-445", "MEGAFAC F-446", "MEGAFAC F-470", "MEGAFAC F-471", "MEGAFAC F-474", "MEGAFAC F-475", "MEGAFAC F-477", "MEGAFAC F-478", "MEGAFAC F-479", "MEGAFAC F-480SF", "MEGAFAC F-482", "MEGAFAC F-483", "MEGAFAC F-484", "MEGAFAC F-486", "MEGAFAC F-487", "MEGAFAC F-489", "MEGAFAC F-172D", "MEGAFAC F-178K", "MEGAFAC F-178RM", "MEGAFAC R-08", "MEGAFAC R-30", "MEGAFAC F-472SF", "MEGAFAC BL-20", "MEGAFAC R-61", "MEGAFAC R-90", "MEGAFAC ESM-1" and "MEGAFAC MCF-350SF" (all manufactured by DIC Corporation), "FTERGENT 100", "FTERGENT 100C", "FTERGENT 110", "FTERGENT 150", "FTERGENT 150CH", "FTERGENT A", "FTERGENT 100A-K", "FTERGENT 501", "FTERGENT 300", "FTERGENT 310", "FTERGENT 320", "FTERGENT 400SW", "FTX-400P", "FTERGENT 251", "FTERGENT 215M", "FTERGENT 212MH", "FTERGENT 250", "FTERGENT 222F", "FTERGENT 212D", "FTX-218", "FTX-209F", "FTX-213F", "FTX-233F", "FTERGENT 245F", "FTX-208G", "FTX-240G", "FTX-206D", "FTX-220D", "FTX-230D", "FTX-240D", "FTX-207S", "FTX-211S", "FTX-220S", "FTX-230S", "FTX-750FM", "FTX-730FM", "FTX-730FL", "FTX-710FS", "FTX-710FM", "FTX-710FL", "FTX-750LL", "FTX-730LS", "FTX-730LM", "FTX-730LL" and "FTX-710LL" (all manufactured by NEOS COMPANY LIMITED), "BYK-300", "BYK-302", "BYK-306", "BYK-307", "BYK-310", "BYK-315", "BYK-320", "BYK-322", "BYK-323", "BYK-325", "BYK-330", "BYK-331", "BYK-333", "BYK-337", "BYK-340", "BYK-344", "BYK-370", "BYK-375", "BYK-377", "BYK-350", "BYK-352", "BYK-354", "BYK-355", "BYK-356", "BYK-358N", "BYK-361N", "BYK-357", "BYK-390", "BYK-392", "BYK-UV3500", "BYK-UV3510", "BYK-UV3570" and "BYK-Silclean 3700" (all manufactured by BYK Japan K. K.), and "TEGO Rad 2100", "TEGO Rad 2200N", "TEGO Rad 2250", "TEGO Rad 2300", "TEGO Rad 2500", "TEGO Rad 2600" and "TEGO Rad 2700" (all manufactured by TEGO).

The weight average molecular weight of the compounds represented by the general formula (VI) is preferably 200 to 100000, more preferably 300 to 10000, and still more preferably 500 to 5000.

The surfactants or the compounds represented by the general formula (VI) may be used singly, or two or more may be used in combination. The surfactants and the compounds represented by the general formula (VI) may be used in combination.

The total content of the surfactant(s) and the compound(s) represented by the general formula (VI) is preferably 0.01 to 1 wt %, and more preferably 0.04 to 0.4 wt % relative to the total weight of the solids in the polymerizable liquid crystal composition of the present embodiment.

<Other Components>

To further enhance the adhesion with respect to the substrate, a chain transfer agent is preferably additionally added to the composition of the present embodiment. Thiol compounds are preferable as the chain transfer agents. Monothiol compounds, dithiol compounds, trithiol compounds and tetrathiol compounds are more preferable, and trithiol compounds are still more preferable. Specifically, those compounds represented by the general formulae (5-1) to (5-12) below are preferable.

The content of the thiol compounds is preferably 0.5 to 7.0 wt %, and more preferably 1.0 to 5.0 wt % relative to the total weight of the solids in the composition.

[Chem. 18]

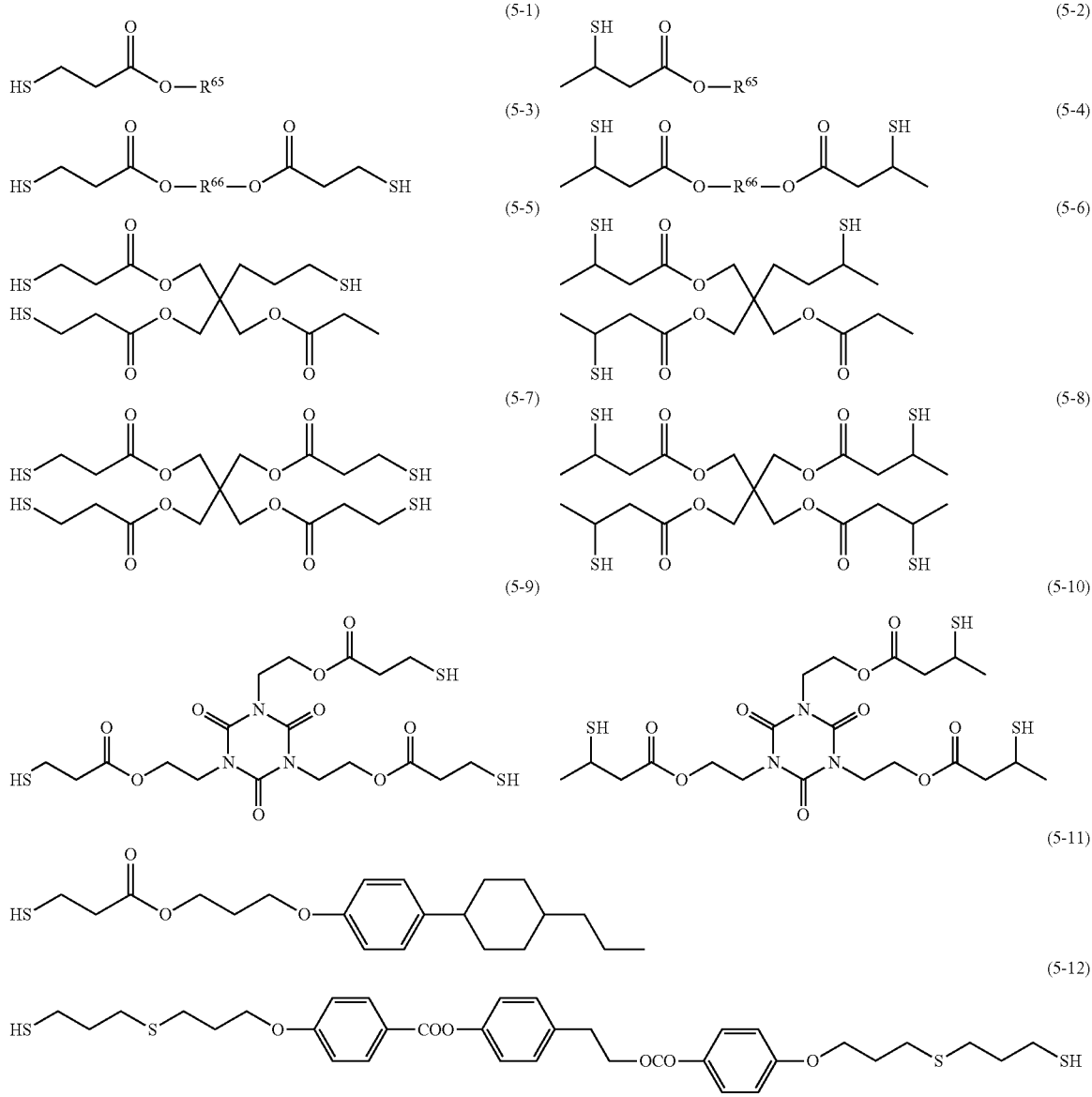

[In the formulae, $R^{65}$ represents an alkyl group having 2 to 18 carbon atoms which may be linear or branched and may be substituted with an oxygen atom, a sulfur atom, —CO—, —OCO—, —COO— or —CH=CH— in place of one or more methylene groups in such a manner that no oxygen atom(s) and/or no sulfur atom(s) are directly bonded to each other, and $R^{66}$ represents an alkylene group having 2 to 18 carbon atoms which may be substituted with an oxygen atom, a sulfur atom, —CO—, —OCO—, —COO— or —CH=CH— in place of one or more methylene groups in such a manner that no oxygen atom(s) and/or no sulfur atom(s) are directly bonded to each other.]

To enhance the storage stability, additives such as polymerization inhibitors and antioxidants are preferably added to the composition of the present embodiment. Examples of such compounds include hydroquinone derivatives and hindered phenol antioxidants. Specific examples include p-methoxyphenol, and IRGANOX 1010, IRGANOX 1035, IRGANOX 1076, IRGANOX 1098, IRGANOX 1135, IRGANOX 1330, IRGANOX 1425, IRGANOX 1520, IRGANOX 1726, IRGANOX 245, IRGANOX 259, IRGANOX 3114, IRGANOX 3790, IRGANOX 5057 and IRGANOX 565 manufactured by BASF.

The content of the polymerization inhibitors and the antioxidants is preferably 0.01 to 1.0 mass %, and more preferably 0.02 to 0.2 mass % relative to the total weight of the solids in the composition.

In order to control properties of the composition of the present embodiment, components such as nonpolymerizable liquid crystal compounds or non-liquid crystalline polymerizable compounds may be added as required.

The content of such compounds is preferably not more than 20 wt %, more preferably not more than 10 wt %, and still more preferably not more than 5 wt % relative to the total weight of the solids in the composition.

<<Polymers, Optically Anisotropic Articles and Liquid Crystal Displays>>

The polymers according to the third embodiment may be obtained by polymerizing the polymerizable compounds of the first embodiment present in the compositions of the second embodiment in accordance with known techniques. The polymers are suited for the production of optically anisotropic articles in the field of liquid crystal displays such as retardation films, patterned retardation films and homogeneously aligned liquid crystal films, and are also suited as antireflection films in organic EL displays.

Hereinbelow, a method for fabricating a retardation film will be described as an example. The polymerizable compound of the first embodiment is used as a solution in a solvent. The solution is applied onto a surface such as the base (substrate) described hereinabove and dried, and the compound is polymerized by a treatment such as UV application or heating to give a retardation film. To facilitate the orientation of the polymerizable compound, an alignment treatment may be performed on the substrate beforehand. In particular, the fabrication of a retardation film may be facilitated by using an optical alignment film as the alignment workpiece. The pattern of retardations may be changed by changing the temperatures at which the solution spread on the substrate is heated.

The liquid crystal display devices according to the fifth embodiment include the optically anisotropic articles of the fourth embodiment, and may be manufactured by incorporating the optically anisotropic articles of the fourth embodiment into liquid crystal display devices in accordance with known techniques.

Next, the present invention will be described in further detail based on Examples. However, the scope of the invention is not limited to such Examples. Unless otherwise mentioned, "parts" and "%" are on the mass basis.

EXAMPLES

Example 1

A polymerizable compound represented by the formula (1-1-15) below was synthesized by the process described below.

[Chem. 19]

(1-1-15)

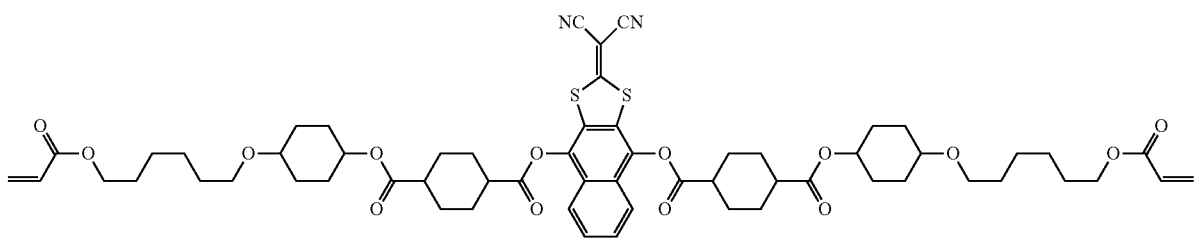

The upper limit temperature for the phase sequence of the polymerizable compound (1-1-15) was determined to be "C 150 N 180 Iso" by differential scanning calorimetry and the observation of the liquid crystal phase with a polarizing microscope equipped with a temperature controller.

<Synthesis Process 1>

The polymerizable compound (1-1-15) was synthesized in accordance with the following scheme.

[Chem. 20]

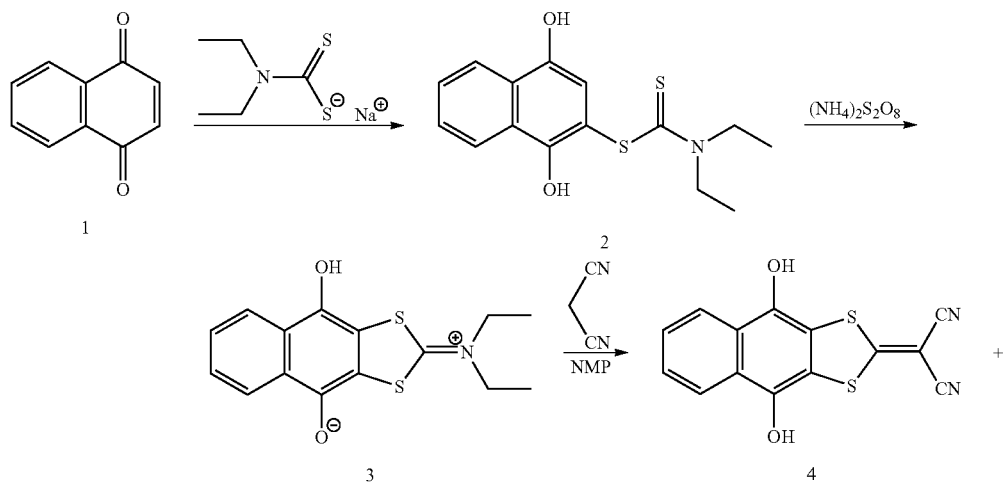

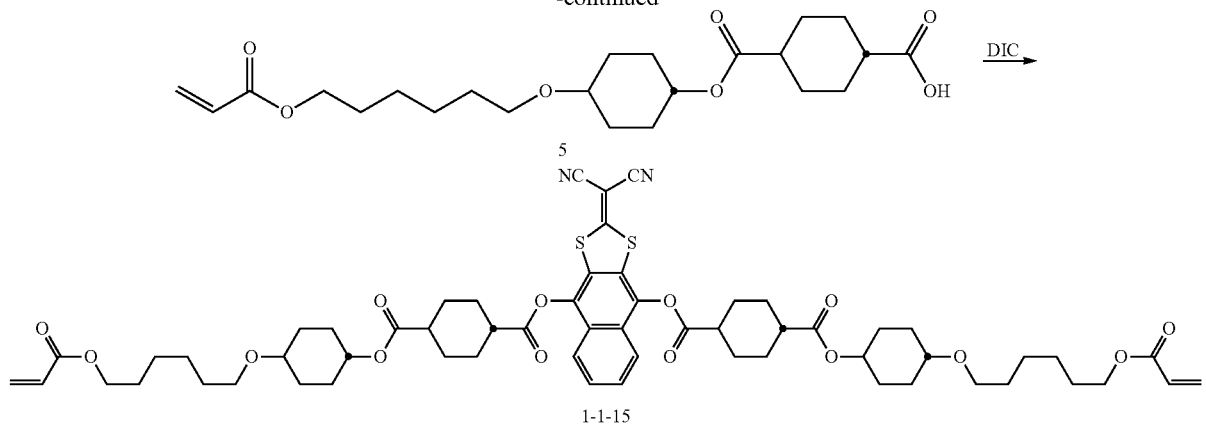

1-1-15

[Exemplary Synthesis of Compound (3)]

In a nitrogen atmosphere, a 300 ml four-necked flask was loaded with 22.5 g (100 mmol) of sodium diethyldithiocarbamate trihydrate, 10 ml of water and 100 ml of methanol. The compound was uniformly dissolved. While keeping the inside temperature at not more than 10° C., a solution containing 15.8 g (100 mmol) of 1,4-naphthoquinone (Compound (1)), 17 ml (300 mmol) of acetic acid and 50 ml of methanol was added dropwise. The mixture was reacted for 30 minutes while performing cooling with ice to give Compound (2). Directly thereafter, a solution of 22.8 g (100 mmol) of ammonium peroxodisulfate in 50 ml of water was added dropwise while keeping the inside temperature at not more than 10° C. The reaction was performed at 50° C. for 2 hours. The resultant solid was filtered off, washed with 100 ml of water and 100 ml of methanol, and dried to give 19.2 g of Compound (3) (yield: 63%).

[Exemplary Synthesis of Compound (4)]

In a nitrogen atmosphere, a 300 ml four-necked flask was loaded with 15.3 g (50 mmol) of Compound (3), 4.0 g (60 mmol) of malononitrile, 50 mg of IRGANOX 1010 (trade name, manufactured by Ciba Specialty Chemicals Inc.) and 100 ml of N-methyl-2-pyrrolidone (NMP). While performing stirring, the mixture was heated to 80° C. After the suspension became a uniform solution, stirring was performed for another 3 hours. After the solution had been cooled to room temperature, ethyl acetate and water were added thereto and the liquid was separated. The organic phase was washed sequentially with water and saturated saline. The organic phase was dried with sodium sulfate. The sodium sulfate was removed by filtration, and the solvent was concentrated under reduced pressure. The concentrated residue was purified by silica gel column chromatography. In this manner, 8.4 g of Compound (4) was obtained (yield: 56%).

Compound (5) was synthesized in accordance with the following scheme.

[Chem. 21]

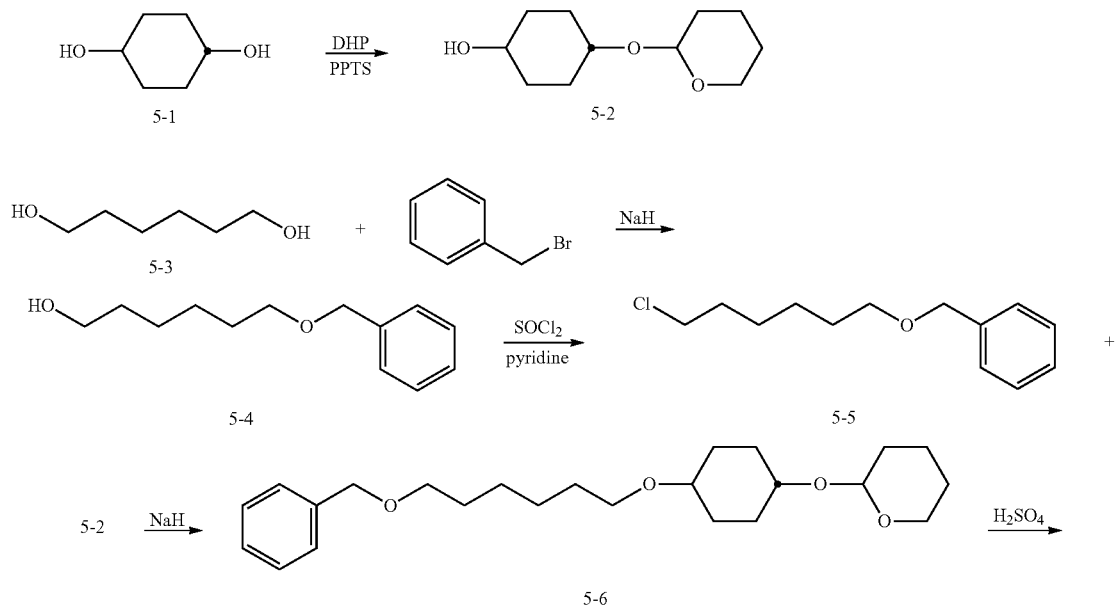

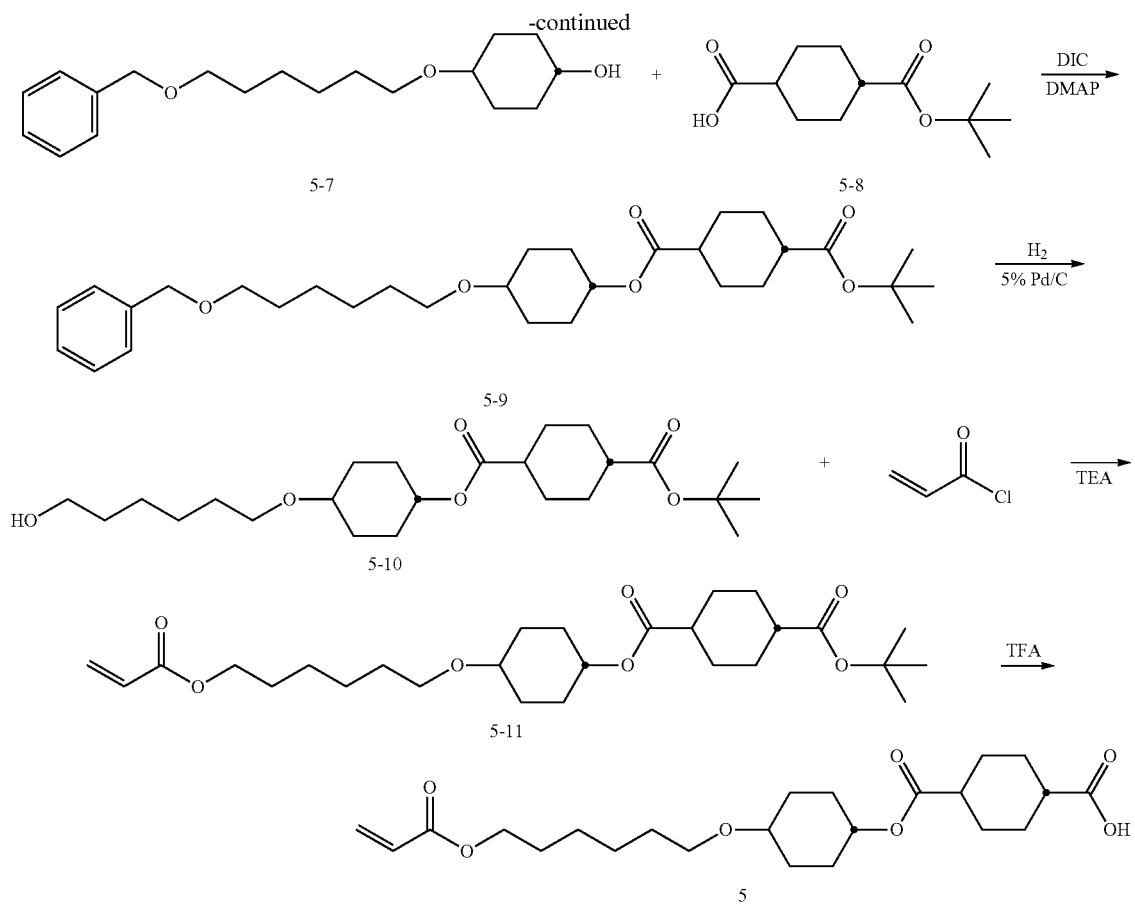

[Exemplary Synthesis of Compound (5-2)]

In a nitrogen atmosphere, a 1000 ml four-necked flask was loaded with 58.1 g (500 mmol) of Compound (5-1), 6.3 g (25 mmol) of pyridinium para-toluenesulfonate (PPTS) and 600 ml of dichloromethane. The mixture was stirred to uniformity. While keeping the inside temperature at not more than 10° C., 21.0 g (250 mmol) of 3,4-dihydro-2H-pyran (DHP) was added dropwise over a period of 1 hour. The mixture was stirred at room temperature for 6 hours. The reaction liquid was washed with a saturated aqueous sodium hydrogen carbonate solution and was dried with sodium sulfate. The sodium sulfate was removed by filtration, and the filtrate was concentrated under reduced pressure. The concentrated residue was purified by silica gel column chromatography. In this manner, 42.1 g of Compound (5-2) was obtained (yield on the basis of DHP: 84%).

[Exemplary Synthesis of Compound (5-4)]

In a nitrogen atmosphere, a 1000 ml four-necked flask was loaded with 300 ml of dimethylformamide (DMF) and 12.0 g of sodium hydride (60%, dispersed in liquid paraffin). The mixture was stirred. While keeping the inside temperature at not more than 10° C., 200 ml of a DMF solution of 70.9 g (600 mmol) of Compound (5-3) was added dropwise. After the generation of hydrogen had ceased, 51.4 g (300 mmol) of benzyl bromide was added dropwise at room temperature. The reaction was performed at 60° C. for 6 hours. After being cooled to room temperature, the reaction liquid was poured into a mixture of 1000 ml of ethyl acetate and 1000 ml of water and the liquid was separated. The organic phase was washed sequentially with water and saturated saline, and was dried with sodium sulfate. The sodium sulfate was removed by filtration, and the filtrate was concentrated under reduced pressure. The concentrated residue was purified by silica gel column chromatography. In this manner, 48.7 g of Compound (5-4) was obtained (yield on the basis of benzyl bromide: 78%).

[Exemplary Synthesis of Compound (5-5)]

In a nitrogen atmosphere, a 1000 ml four-necked flask was loaded with 45.0 g (216 mmol) of Compound (5-4), 18.8 g (238 mmol) of pyridine and 500 ml of dichloromethane. The mixture was stirred to uniformity. While keeping the inside temperature at not more than 10° C., 27.0 g (227 mmol) of thionyl chloride was added dropwise. After the dropwise addition, the reaction was performed at room temperature for 6 hours. 500 ml of water was added to the reaction liquid and the liquid was separated. The organic phase was washed sequentially with water and saturated saline, and was dried with sodium sulfate. The sodium sulfate was removed by filtration, and the filtrate was concentrated under reduced pressure. The concentrated residue was purified by silica gel column chromatography. In this manner, 47.5 g of Compound (5-5) was obtained (yield: 97%).

[Exemplary Synthesis of Compound (5-6)]

In a nitrogen atmosphere, a 500 ml four-necked flask was loaded with 300 ml of dimethylformamide (DMF) and 8.9 g of sodium hydride (60%, dispersed in liquid paraffin). The mixture was stirred. While keeping the inside temperature at not more than 10° C., 100 ml of a DMF solution of 40.7 g (203 mmol) of Compound (5-2) was added dropwise. After the generation of hydrogen had ceased, 46.0 g (203 mmol) of Compound (5-5) was added dropwise at room temperature. The reaction was performed at 60° C. for 6 hours. After being cooled to room temperature, the reaction liquid was poured into a mixture of 500 ml of ethyl acetate and 500 ml of water and the liquid was separated. The organic phase was washed sequentially with water and saturated saline, and was dried with sodium sulfate. The sodium sulfate was removed by filtration, and the filtrate was concentrated under reduced pressure. The concentrated residue was purified by silica gel column chromatography. In this manner, 65.2 g of Compound (5-6) was obtained (yield: 82%).

[Synthesis of Compound (5-7)]

A 500 ml four-necked flask was loaded with 63.0 g (161 mmol) of Compound (5-6), 250 ml of tetrahydrofuran (THF) and 50 ml of methanol. The mixture was stirred. To the mixed liquid, 1.0 g of concentrated sulfuric acid was added. The reaction was performed at room temperature for 5 hours. The reaction liquid was poured into 500 ml of ethyl acetate, and the liquid was washed sequentially with a saturated aqueous sodium hydrogen carbonate solution and saturated saline. The organic phase was concentrated, and the residue was purified by silica gel column chromatography. In this manner, 45.3 g of Compound (5-7) was obtained (yield: 92%).

[Synthesis of Compound (5-8)]

Compound (5-8) was synthesized by the process described below.

[Chem. 22]

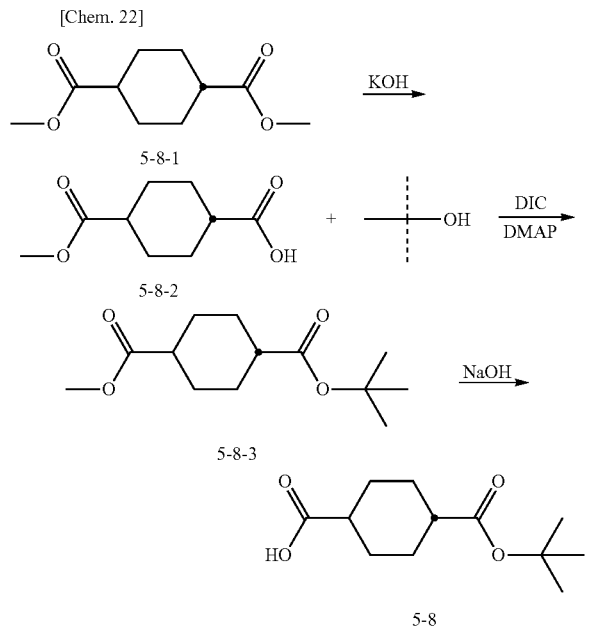

[Synthesis of Compound (5-8-2)]

A four-necked flask (1 l) was loaded with 100.0 g (500 mmol) of dimethyl trans-1,4-cyclohexanedicarboxylate ester (5-8-1) and 1000 ml of methanol. The mixture was stirred. After 16.8 g (300 mmol) of potassium hydroxide had been added, the reaction was performed under reflux for 6 hours. After being cooled, the reaction liquid was concentrated and 500 ml of water was added to the residue. Diluted hydrochloric acid was added until the pH became 2, and the crystal precipitated was filtered off. The crystal was washed with water and was dried under reduced pressure. In this manner, 54.0 g of Compound (5-8-2) was obtained (yield: 58.0%).

[Synthesis of Compound (5-8-3)]

In a nitrogen atmosphere, a 300 ml four-necked flask was loaded with 49.5 g (266 mmol) of Compound (5-8-2), 3.3 g (26.7 mmol) of N,N-dimethyl-4-aminopyridine (DMAP), 150 ml of tert-butyl alcohol and 150 ml of tetrahydrofuran. The mixture was stirred to uniformity. While performing cooling with ice, 50.4 g (399 mmol) of N,N'-diisopropylcarbodiimide (DIC) was added dropwise. The reaction was performed at room temperature for 6 hours. After the addition of 15 ml of water, the mixture was stirred for 1 hour. The insoluble was removed by filtration, and the reaction liquid was concentrated under reduced pressure. The residue obtained was purified by silica gel column chromatography (dichloromethane). In this manner, 51.9 g of Compound (5-8-3) was obtained (yield: 80.6%).

[Synthesis of Compound (5-8)]

A four-necked flask (300 ml) was loaded with 48.0 g (198 mmol) of Compound (5-8-3), 150 ml of methanol and 150 ml of tetrahydrofuran. The mixture was stirred. While performing cooling with ice, 24.0 g (600 mmol) of sodium hydroxide was added. The mixture was stirred at not more than 5° C. for 3 hours. The mixture was poured into 1000 ml of water and was washed with dichloromethane. Diluted hydrochloric acid was added to the aqueous phase until the pH became 2. The crystal precipitated was filtered off, washed with water and dried under reduced pressure. In this manner, 41.4 g of Compound (5-8) was obtained (yield: 91.6%).

[Synthesis of Compound (5-9)]

In a nitrogen atmosphere, a 300 ml four-necked flask was loaded with 44.0 g (144 mmol) of Compound (5-7), 32.8 g (144 mmol) of Compound (5-8), 1.8 g (14.4 mmol) of N,N-dimethyl-4-aminopyridine (DMAP) and 500 ml of tetrahydrofuran. The mixture was stirred to uniformity. While performing cooling with ice, 20.0 g (158 mmol) of N,N'-diisopropylcarbodiimide (DIC) was added dropwise. The reaction was performed at room temperature for 6 hours. After the addition of 15 ml of water, the mixture was stirred for 1 hour. The insoluble was removed by filtration, and the reaction liquid was concentrated under reduced pressure. The residue obtained was purified by silica gel column chromatography (dichloromethane). In this manner, 69.2 g of Compound (5-9) was obtained (yield: 93%).

[Synthesis of Compound (5-10)]

A 1 l autoclave was loaded with 68.0 g (132 mmol) of Compound (5-9), 2.8 g of a catalyst (5% Pd/C) and 400 ml of ethyl acetate. While keeping the hydrogen pressure at 0.3 MPa, the reaction was performed at room temperature for 3 hours. The catalyst was removed by filtration, and the filtrate was concentrated under reduced pressure. In this manner, 56.3 g of Compound (5-10) was obtained (quantitative).

[Synthesis of Compound (5-11)]

In a dry air atmosphere, a 500 ml four-necked flask was loaded with 55.0 g (129 mmol) of Compound (5-10), 14.4 g (142 mmol) of triethylamine (TEA) and 300 ml of dichloromethane. The mixture was stirred. 12.3 g (135 mmol) of acryloyl chloride was added dropwise at not more than 5° C. The reaction was performed at room temperature for 3 hours. The reaction liquid was washed sequentially with water, diluted hydrochloric acid, saturated sodium hydrogen carbonate and saturated saline. The organic phase was dried with sodium sulfate. The sodium sulfate was removed by filtration, and the filtrate was concentrated under reduced pressure. In this manner, 62.0 g of Compound (5-11) was obtained (quantitative).

[Synthesis of Compound (5)]

In a dry air atmosphere, a 2000 ml four-necked flask was loaded with 60.0 g (125 mmol) of Compound (5-11) and 1000 ml of dichloromethane. The mixture was stirred. While performing cooling with ice, 142 g (1250 mmol) of trifluoroacetic acid (TFA) was added dropwise. The reaction was performed at room temperature for 8 hours. 1000 ml of hexane was added, and the dichloromethane was distilled away under reduced pressure. The crystal precipitated was filtered off and was washed sequentially with water and hexane. The crystal was then dried under reduced pressure. In this manner, 51.0 g of Compound (5) was obtained (yield: 96.1%).

[Synthesis of Compound (1-1-15)]

In a nitrogen atmosphere, a 300 ml four-necked flask was loaded with 3.3 g (11 mmol) of Compound (4), 10.2 g (24 mmol) of Compound (5), 0.28 g (2 mmol) of N,N-dimethyl-4-aminopyridine (DMAP) and 80 ml of dichloromethane. The mixture was stirred. To the resultant mixed liquid, 20 ml of a dichloromethane solution of 3.2 g (25 mmol) of diisopropylcarbodiimide (DIC) was added dropwise at not more than 5° C. After the dropwise addition, the reaction was performed at room temperature for 4 hours. 1 ml of water was added, and the mixture was stirred for 1 hour. The insoluble was removed by filtration, and the filtrate was washed with water and dried with sodium sulfate. The sodium sulfate was removed by filtration, and the filtrate was concentrated under reduced pressure. 200 ml of methanol was added to the residue. The resultant mixture was cooled with ice to cause precipitation. The precipitate was filtered off and was washed sequentially with methanol and n-hexane. The product was dried under reduced pressure to give 8.8 g of Compound (1-15-1) (yield: 72%).

<Fabrication of Optical Film>

A coating liquid was prepared which contained 19.32 wt % of the polymerizable compound (1-1-15) synthesized above, 0.60 wt % of IRGACURE 907 (manufactured by Ciba Specialty Chemicals Inc.) as a polymerization initiator, 0.04 wt % of p-methoxyphenol (MEHQ) as a polymerization inhibitor, 0.04 wt % of BYK-361N (manufactured by BYK Japan K. K.) as a surfactant and 80.00 wt % of chloroform as a solvent.

Next, a glass substrate having a rubbed polyimide layer was spin coated with the coating liquid. The wet film was dried on a hot plate at 80° C. for 1 minute and at 170° C. for 1 minute, and was UV irradiated at 160° C. and 1000 mJ/cm$^2$. In this manner, an optical film (an optically anisotropic article) was fabricated.

<Measurement of Optical Characteristics>

The optical film fabricated was analyzed to determine the retardations at wavelengths in the range of 450 nm to 700 nm with use of a device (RET-100 manufactured by OTSUKA ELECTRONICS Co., LTD). With a program installed in the device, the retardation Re (450) at 450 nm wavelength, the retardation Re (550) at 550 nm wavelength and the retardation Re (650) at 650 nm wavelength were calculated. The results are described in Table 1.

TABLE 1

|  | Re (450)/Re (550) | Re (650)/Re (550) |
| --- | --- | --- |
| EX. 1 | 0.83 | 1.05 |
| EX. 2 | 0.83 | 1.06 |
| COMP. EX. 1 | 0.86 | 1.03 |
| EX. 3 | 0.84 | 1.04 |
| COMP. EX. 2 | 0.89 | 1.02 |
| EX. 4 | — | 1.15 |
| COMP. EX. 3 | — | 1.12 |

Example 2

A polymerizable compound represented by the formula (1-1-16) below was synthesized by the process described below.

[Chem. 23]

(1-1-16)

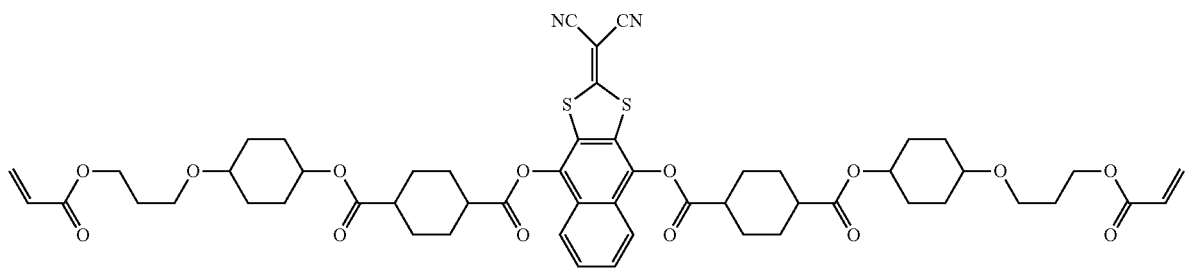

The upper limit temperature for the phase sequence of the polymerizable compound (1-1-16) was determined to be "C 145 N 183 Iso" by differential scanning calorimetry and the observation of the liquid crystal phase with a polarizing microscope equipped with a temperature controller.

<Synthesis Process 2>

[Synthesis of Compound (1-1-16)]

The synthesis was performed in the same manner as in the exemplary synthesis of Compound (1-1-15), except that Compound (5-3) (1,6-hexanediol) was replaced by 1,3-propanediol.

<Fabrication of Optical Film>

A coating liquid was prepared in the same manner as in EXAMPLE 1, except that the polymerizable compound (1-1-15) used in EXAMPLE 1 was replaced by the equal amount of the polymerizable compound (1-1-16).

Next, a glass substrate having a rubbed polyimide layer was spin coated with the coating liquid. The wet film was dried on a hot plate at 80° C. for 1 minute and at 170° C. for 1 minute, and was UV irradiated at 160° C. and 1000 mJ/cm$^2$. In this manner, an optical film (an optically anisotropic article) was fabricated.

<Measurement of Optical Characteristics>

The optical film fabricated was analyzed in the same manner as in EXAMPLE 1 to measure the optical characteristics. The results are described in Table 1.

Comparative Example 1

A polymerizable compound represented by the formula (Ref 1) below was synthesized by the process described below.

[Chem. 24]

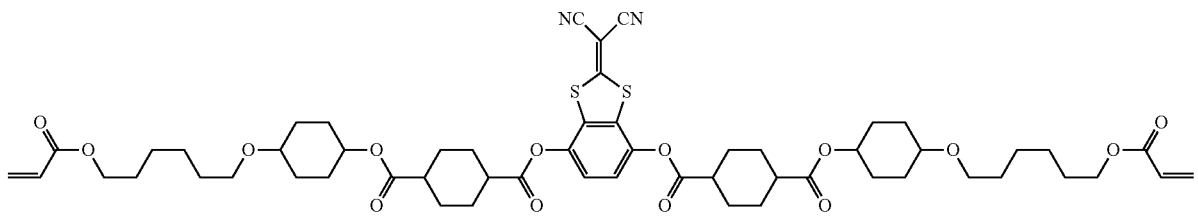

(Ref1)

The upper limit temperature for the phase sequence of the polymerizable compound (Ref 1) was determined to be "C 170 N 206 Iso" by differential scanning calorimetry and the observation of the liquid crystal phase with a polarizing microscope equipped with a temperature controller.

<Synthesis Process 3>

[Synthesis in Comparative Example 1 (Ref 1)]

The synthesis was performed in the same manner as in the exemplary synthesis of Compound (1-1-15), except that Compound (1) (1,4-naphthoquinone) was replaced by 1,4-benzoquinone.

<Fabrication of Optical Film>

A coating liquid was prepared in the same manner as in EXAMPLE 1, except that the polymerizable compound (1-1-15) used in EXAMPLE 1 was replaced by the equal amount of the polymerizable compound (Ref 1).

Next, a glass substrate having a rubbed polyimide layer was spin coated with the coating liquid. The wet film was dried on a hot plate at 80° C. for 1 minute and at 200° C. for 1 minute, and was UV irradiated at 190 C and 1000 mJ/cm$^2$. In this manner, an optical film (an optically anisotropic article) was fabricated.

<Measurement of Optical Characteristics>

The optical film fabricated was analyzed in the same manner as in EXAMPLE 1 to measure the optical characteristics. The results are described in Table 1.

Example 3

A polymerizable compound represented by the formula (1-1-17) below was synthesized by the process described below.

[Chem. 25]

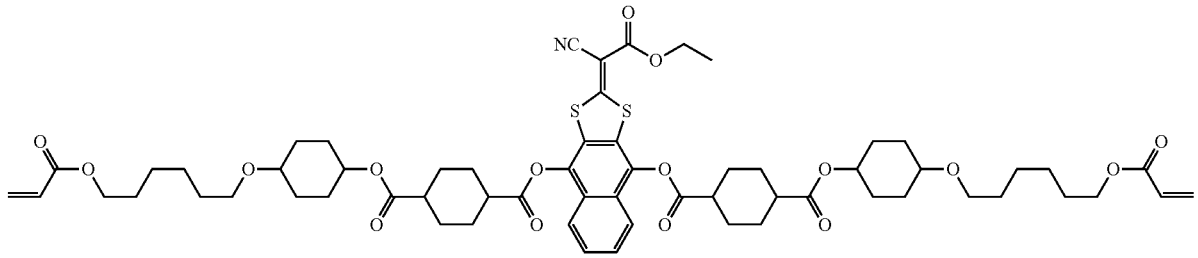

(1-1-17)

The upper limit temperature for the phase sequence of the polymerizable compound (1-1-17) was determined to be "C 88 N 94 Iso" by differential scanning calorimetry and the observation of the liquid crystal phase with a polarizing microscope equipped with a temperature controller.

<Synthesis Process 4>

[Synthesis of Compound (1-1-17)]

The synthesis was performed in the same manner as in the exemplary synthesis of Compound (1-1-15), except that malononitrile used in the exemplary synthesis of Compound (4) was replaced by ethyl cyanoacetate.

<Fabrication of Optical Film>

A coating liquid was prepared in the same manner as in EXAMPLE 1, except that the polymerizable compound (1-1-15) used in EXAMPLE 1 was replaced by the equal amount of the polymerizable compound (1-1-17).

Next, a glass substrate having a rubbed polyimide layer was spin coated with the coating liquid. The wet film was dried on a hot plate at 80° C. for 1 minute and at 90° C. for 1 minute, and was UV irradiated at 90° C. and 1000 mJ/cm². In this manner, an optical film (an optically anisotropic article) was fabricated.

<Measurement of Optical Characteristics>

The optical film fabricated was analyzed in the same manner as in EXAMPLE 1 to measure the optical characteristics. The results are described in Table 1.

Comparative Example 2

A polymerizable compound represented by the formula (Ref 2) below was synthesized by the process described below.

[Chem. 26]

The upper limit temperature for the phase sequence of the polymerizable compound (Ref 2) was determined to be "C 105 N 117 Iso" by differential scanning calorimetry and the observation of the liquid crystal phase with a polarizing microscope equipped with a temperature controller.

<Synthesis Process 5>

[Synthesis in Comparative Example 2 (Ref 2)]

The synthesis was performed in the same manner as in the exemplary synthesis of Compound (1-1-15), except that Compound (1) (1,4-naphthoquinone) was replaced by 1,4-benzoquinone and that malononitrile used in the exemplary synthesis of Compound (4) was replaced by ethyl cyanoacetate.

<Fabrication of Optical Film>

A coating liquid was prepared in the same manner as in EXAMPLE 1, except that the polymerizable compound (1-1-15) used in EXAMPLE 1 was replaced by the equal amount of the polymerizable compound (Ref 2).

Next, a glass substrate having a rubbed polyimide layer was spin coated with the coating liquid. The wet film was dried on a hot plate at 80° C. for 1 minute and at 110° C. for 1 minute, and was UV irradiated at 110° C. and 1000 mJ/cm². In this manner, an optical film (an optically anisotropic article) was fabricated.

<Measurement of Optical Characteristics>

The optical film fabricated was analyzed in the same manner as in EXAMPLE 1 to measure the optical characteristics. The results are described in Table 1.

Example 4

A polymerizable compound represented by the formula (1-1-18) below was synthesized by the process described below.

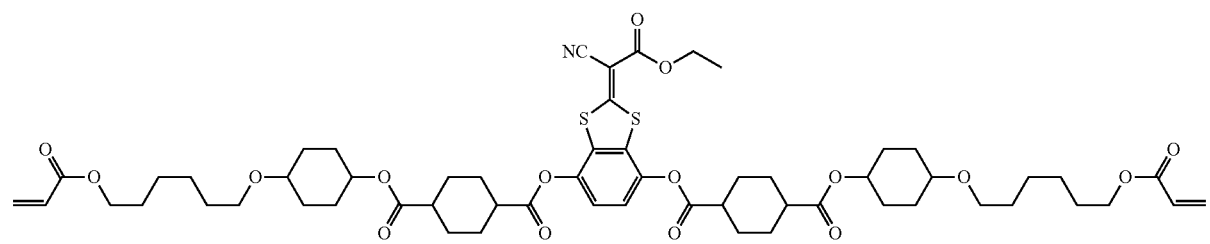

(Ref2)

[Chem.27]

(1-1-18)

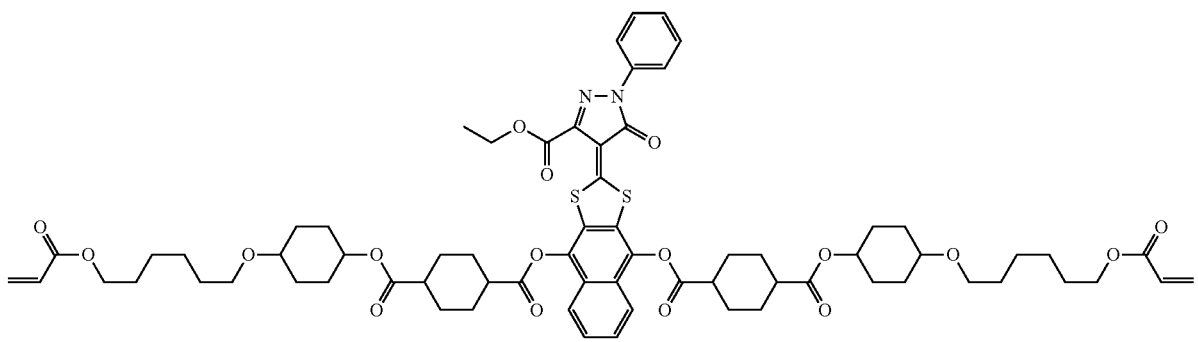

The upper limit temperature for the phase sequence of the polymerizable compound (1-1-18) was determined to be "C 125 N 137 Iso" by differential scanning calorimetry and the observation of the liquid crystal phase with a polarizing microscope equipped with a temperature controller.
<Synthesis Process 6>
[Synthesis of Compound (1-1-18)]
The synthesis was performed in the same manner as in the exemplary synthesis of Compound (1-1-15), except that malononitrile used in the exemplary synthesis of Compound (4) was replaced by ethyl 5-oxo-1-phenyl-2-pyrazoline-3-carboxylate.

[Chem. 28]

<Fabrication of Optical Film>

A coating liquid was prepared in the same manner as in EXAMPLE 1, except that the polymerizable compound (1-1-15) used in EXAMPLE 1 was replaced by the equal amount of the polymerizable compound (1-1-18).

Next, a glass substrate having a rubbed polyimide layer was spin coated with the coating liquid. The wet film was dried on a hot plate at 80° C. for 1 minute and at 130° C. for 1 minute, and was UV irradiated at 130° C. and 1000 mJ/cm². In this manner, an optical film (an optically anisotropic article) was fabricated.

<Measurement of Optical Characteristics>

The optical film fabricated was analyzed in the same manner as in EXAMPLE 1 to measure the optical characteristics. The results are described in Table 1.

Comparative Example 3

A polymerizable compound represented by the formula (Ref 3) below was synthesized by the process described below.

(Ref3)

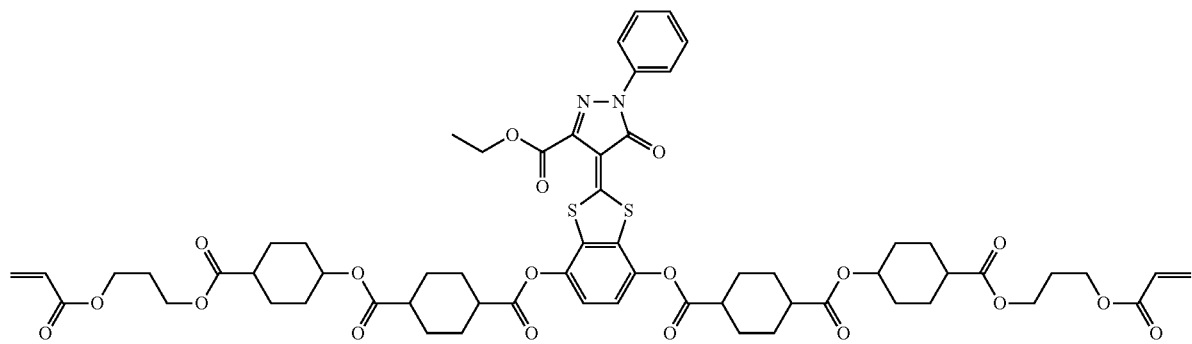

The upper limit temperature for the phase sequence of the polymerizable compound (Ref 3) was determined to be "C 145 N 187 Iso" by differential scanning calorimetry and the observation of the liquid crystal phase with a polarizing microscope equipped with a temperature controller.
<Synthesis Process 5>
[Synthesis in Comparative Example 3 (Ref 3)]
The synthesis was performed in the same manner as in the exemplary synthesis of Compound (1-1-15), except that Compound (1) (1,4-naphthoquinone) was replaced by 1,4-benzoquinone, that malononitrile used in the exemplary synthesis of Compound (4) was replaced by ethyl 5-oxo-1-phenyl-2-pyrazoline-3-carboxylate, and that Compound (5-3) (1,6-hexanediol) was replaced by 1,3-propanediol.
<Fabrication of Optical Film>
A coating liquid was prepared in the same manner as in EXAMPLE 1, except that the polymerizable compound (1-1-15) used in EXAMPLE 1 was replaced by the equal amount of the polymerizable compound (Ref 3).

Next, a glass substrate having a rubbed polyimide layer was spin coated with the coating liquid. The wet film was dried on a hot plate at 80° C. for 1 minute and at 150° C. for 1 minute, and was UV irradiated at 150° C. and 1000 mJ/cm². In this manner, an optical film (an optically anisotropic article) was fabricated.

<Measurement of Optical Characteristics>

The optical film fabricated was analyzed in the same manner as in EXAMPLE 1 to measure the optical characteristics. The results are described in Table 1.

As demonstrated above, the polymerizable compounds of EXAMPLES 1 to 4 achieved enhanced reverse wavelength dispersion properties as compared to the polymerizable compounds of COMPARATIVE EXAMPLES. It has been thus shown that the use of the polymerizable compounds of EXAMPLES 1 to 4 makes it possible to produce optically anisotropic articles having excellent optical characteristics.

One of the reasons as to why the optical films of EXAMPLES 1 to 4 exhibit excellent characteristics is probably because the incorporation of naphthalene rings into the vertical units results in an increase in the wavelength dispersion along the shorter molecular axis and thus contributes to the enhancement in optical characteristics.

The features described in the aforementioned embodiments such as configurations and combinations of the configurations are only illustrative. It is therefore possible to add other configurations or to omit, replace or modify the configurations described herein without departing from the spirit of the invention. The scope of the invention is not limited to the embodiments described hereinabove and is limited only by the claims.

INDUSTRIAL APPLICABILITY

The polymerizable compounds according to the present invention may be widely applied to the field of liquid crystal displays.

The invention claimed is:

1. A polymerizable compound represented by the general formula selected from the group consisting of (1-1), (1-2) and (1-3):

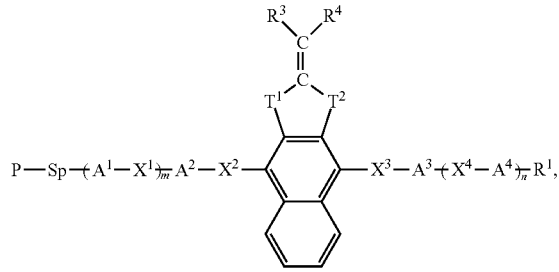
(1-1)

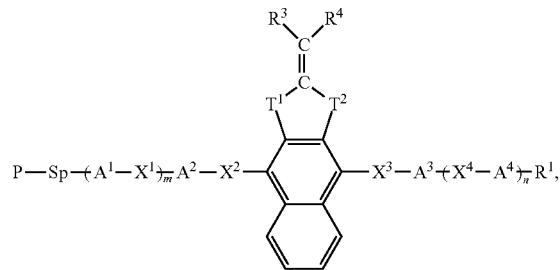
(1-2)

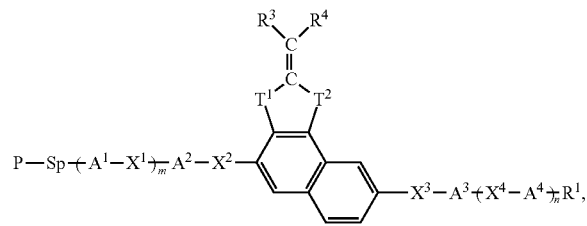
(1-3)

wherein in the formulae (1-1), (1-2) and (1-3), P is a polymerizable functional group, Sp is a spacer group or a single bond, $A^1$, $A^2$, $A^3$ and $A^4$ each independently represent a divalent alicyclic hydrocarbon group or aromatic hydrocarbon group, $X^1$, $X^2$, $X^3$ and $X^4$ each independently represent a divalent bonding group or a single bond, $R^1$ is an alkyl or alkoxy group having 1 to 12 carbon atoms, or "*-Sp-P" in which * indicates $A^4$ or $A^3$, m and n are each independently an integer of 0 to 4 wherein m+n is an integer of 2 or greater, $T^1$ and $T^2$ each independently represent —S—, —O—, —NR²—, —CH$_2$—, —NH—, —C(=O)—, —S(=O)— or —C(=S)—, $R^2$ is a hydrogen atom, a halogen atom, an alkyl group having 1 to 6 carbon atoms, an alkoxy group having 1 to 6 carbon atoms, a cyano group, a nitro group or a hydroxyl group, $R^3$ and $R^4$ each independently represent a monovalent substituent or form a ring through Y which connects $R^3$ and $R^4$ together wherein when such a ring is formed, $R^3$ and $R^4$ each independently represent a group selected from the group consisting of —O—, —S—, —SO—, —SO$_2$—, —NR— wherein R is a hydrogen atom or a monovalent substituent, =N—, =N(+)R— wherein R of =N(+)R— is a hydrogen atom or a monovalent substituent, —C(=O)—, —C(=S)— and =CR— wherein R of =CR— is a hydrogen atom or a monovalent substituent, and Y represents 2 to 4 atoms selected from the group consisting of carbon atoms and Group XIV to Group XVI nonmetallic atoms, and in combination with $R^3$—C—$R^4$ in the formula forms a 5- to 7-membered ring which may be substituted with a monovalent substituent in place of any hydrogen atom bonded to the 5- to 7-membered ring, except when $T^1$ and $R^3$, and $T^2$ and $R^4$ are each the same as each other and when $T^1$ and $R^4$, and $T^2$ and $R^3$ are each the same as each other.

2. The polymerizable compound according to claim 1, wherein $R^3$ and $R^4$ are each independently a monovalent substituent and at least one of $R^3$ and $R^4$ is a cyano group.

3. The polymerizable compound according to claim 1, wherein $R^3$ and $R^4$ are each independently a monovalent substituent and $R^3$ or $R^4$ is an alkyl carboxylate having an alkyl group with 1 to 3 carbon atoms.

4. The polymerizable compound according to claim 1, wherein the ring formed by $R^3$—C—$R^4$ and Y is any selected from the group consisting of rings represented by the following general formulae (Y-1) to (Y-24):

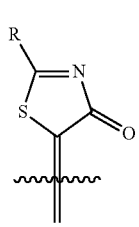
(Y1)

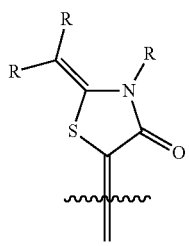
(Y2)

(Y3)

(Y4)

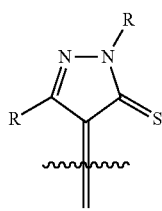
(Y5)

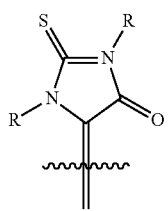

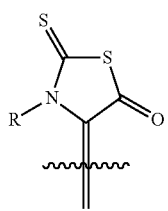

-continued

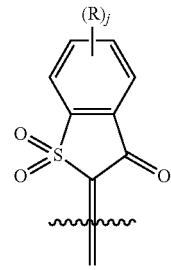
(Y6)

(Y7)

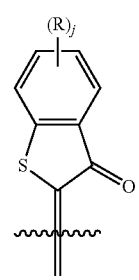
(Y8)

(Y9)

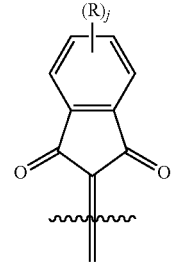
(Y10)

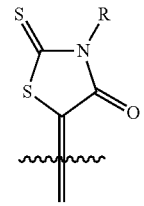
(Y11)

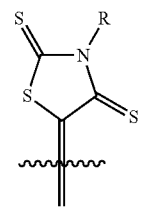

-continued (Y12) 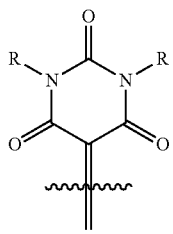

(Y13) 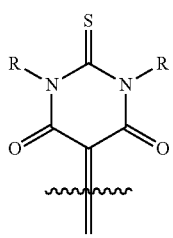

(Y14) 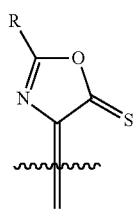

(Y15) 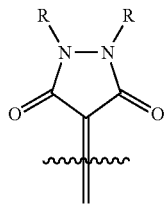

(Y16) 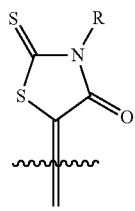

(Y17) 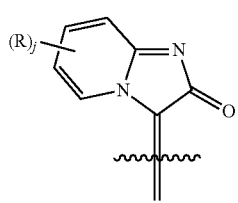

(Y18) 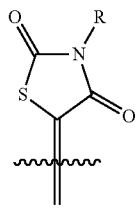

-continued (Y19) 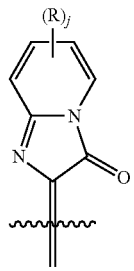

(Y20) 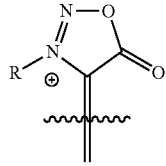

(Y21) 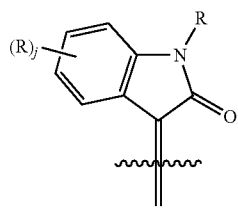

(Y22) 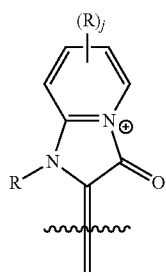

(Y23) 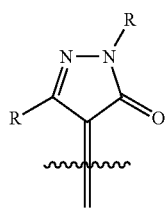

(Y24) 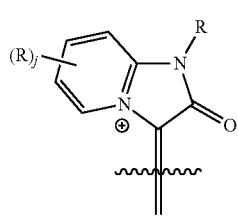

in the formulae, R is a hydrogen atom or a monovalent substituent, j is an integer of 0 to 4, and the bonds =C intersected with a wiggly line are to the 5-membered ring including $T^1$ and $T^2$ in the general formula (1-0).

5. The polymerizable compound according to claim 1, wherein $X^1$, $X^2$, $X^3$ and $X^4$ each independently represent a single bond, —CH$_2$CH$_2$—, —CH=CH—, —CH=CHCOO—, —OCO—CH=CH—, —(CH$_2$)$_u$O—COO—, —(CH$_2$)$_u$—OCO—, —(CH$_2$)$_u$—COO—, —$(CH_2)_u$—O—, —O—COO—$(CH_2)_u$—, —OCO—$(CH_2)_u$—, —COO—$(CH_2)_u$— or —O—$(CH_2)_u$— wherein u is an integer of 0 to 2.

6. A composition comprising the polymerizable compound described in claim 1.

7. A polymer obtained by polymerizing the composition described in claim 6.

8. An optically anisotropic article comprising the polymer described in claim 7.

9. A liquid crystal display device comprising the optically anisotropic article described in claim 8.

10. An organic EL device comprising the optically anisotropic article described in claim 8.

* * * * *